(12) United States Patent
Lim

(10) Patent No.: US 10,499,984 B2
(45) Date of Patent: Dec. 10, 2019

(54) APPARATUS AND METHOD FOR ASSESSING TISSUE TREATMENT

(71) Applicant: Bernard Boon Chye Lim, Springfield, IL (US)

(72) Inventor: Bernard Boon Chye Lim, Springfield, IL (US)

( * ) Notice: Subject to any disclaimer, the term of this patent is extended or adjusted under 35 U.S.C. 154(b) by 0 days.

(21) Appl. No.: 15/343,622

(22) Filed: Nov. 4, 2016

(65) Prior Publication Data

US 2017/0071664 A1    Mar. 16, 2017

Related U.S. Application Data

(63) Continuation-in-part of application No. 13/945,749, filed on Jul. 18, 2013, now Pat. No. 9,526,426.

(Continued)

(51) Int. Cl.
*A61B 18/14* (2006.01)
*A61B 18/02* (2006.01)
(Continued)

(52) U.S. Cl.
CPC ........ *A61B 18/1492* (2013.01); *A61B 5/0044* (2013.01); *A61B 5/0073* (2013.01);
(Continued)

(58) Field of Classification Search
CPC ... A61B 18/1492; A61B 5/6855; A61B 34/20; A61B 5/0084; A61B 5/0044; A61B 5/6858; A61B 5/6857; A61B 18/24; A61B 5/0075; A61B 5/0073; A61B 18/02; A61B 2090/3966; A61B 2034/2048; A61B 2018/00982; A61B 2018/0022; A61B 2018/00351; A61B 2018/1467; A61B 2018/00577; A61B 2018/00642; A61B 2018/0212; A61B 2018/00267; A61N 7/00; A61N 2007/0043
(Continued)

(56) References Cited

U.S. PATENT DOCUMENTS 4,830,014 A    5/1989   Goodman et al.
5,041,109 A    8/1991   Abela
(Continued)

FOREIGN PATENT DOCUMENTS

WO    WO 2009/124301    10/2009

OTHER PUBLICATIONS

Agah, R. et al., IEEE Transactions on Biomedical Engineering, Aug. 1996, pp. 839-846, vol. 43 No. 8 (see p. 842-844) Inst. Elect. & Electronics US.
(Continued)

*Primary Examiner* — Sanjay Cattungal
(74) *Attorney, Agent, or Firm* — John M. Berns

(57) ABSTRACT

The invention relates to a tissue monitoring apparatus, a tissue monitoring method and an ablation lesion monitoring, measuring, and controlling automated algorithm incorporating diffuse reflectance spectroscopy (DRS) and/or Arrhenius model thermal denaturation kinetics for determining the characteristics of the lesion or the tissue, especially for identifying the transmurality of the ablation lesion. The invention pertains to a device for and method of real time monitoring of lesion formation as ablation is being carried out.

21 Claims, 25 Drawing Sheets

Related U.S. Application Data

(60) Provisional application No. 61/673,025, filed on Jul. 18, 2012.

(51) Int. Cl.

| | | |
|---|---|---|
| *A61B 5/00* | (2006.01) | |
| *A61N 7/00* | (2006.01) | |
| *A61B 18/24* | (2006.01) | |
| *A61B 34/20* | (2016.01) | |
| *A61B 18/00* | (2006.01) | |
| *A61B 90/00* | (2016.01) | |

(52) U.S. Cl.
CPC .......... *A61B 5/0075* (2013.01); *A61B 5/0084* (2013.01); *A61B 5/6855* (2013.01); *A61B 5/6857* (2013.01); *A61B 5/6858* (2013.01); *A61B 18/24* (2013.01); *A61B 18/02* (2013.01); *A61B 34/20* (2016.02); *A61N 7/00* (2013.01); *A61B 2018/0022* (2013.01); *A61B 2018/00267* (2013.01); *A61B 2018/00351* (2013.01); *A61B 2018/00577* (2013.01); *A61B 2018/00642* (2013.01); *A61B 2018/00982* (2013.01); *A61B 2018/0212* (2013.01); *A61B 2018/1467* (2013.01); *A61B 2034/2048* (2016.02); *A61B 2090/3966* (2016.02); *A61N 2007/0043* (2013.01)

(58) Field of Classification Search
USPC .................................................. 600/437–480
See application file for complete search history.

(56) References Cited

U.S. PATENT DOCUMENTS

| | | | | |
|---|---|---|---|---|
| 5,298,026 | A | | 3/1994 | Chang |
| 5,452,723 | A | * | 9/1995 | Wu ..................... A61B 5/0059 250/339.01 |
| 5,643,251 | A | | 7/1997 | Hillsman et al. |
| 5,647,870 | A | | 7/1997 | Kordis et al. |
| 5,651,785 | A | | 7/1997 | Abela et al. |
| 5,693,043 | A | | 12/1997 | Kittrell et al. |
| 5,762,609 | A | | 6/1998 | Benaron et al. |
| 5,904,651 | A | * | 5/1999 | Swanson ............... A61B 5/0084 600/342 |
| 6,178,346 | B1 | | 1/2001 | Amundson et al. |
| 6,219,566 | B1 | | 4/2001 | Weersink et al. |
| 6,690,966 | B1 | | 2/2004 | Rava et al. |
| 7,232,437 | B2 | | 6/2007 | Berman et al. |
| 7,238,180 | B2 | | 7/2007 | Mester et al. |
| 7,255,695 | B2 | | 8/2007 | Falwell et al. |
| 7,662,152 | B2 | | 2/2010 | Sharareh et al. |
| 7,850,685 | B2 | * | 12/2010 | Kunis ................ A61B 18/1815 606/41 |
| 7,952,719 | B2 | | 5/2011 | Brennan |
| 8,048,063 | B2 | | 11/2011 | Aeby et al. |
| 8,052,605 | B2 | | 11/2011 | Muller et al. |
| 8,078,268 | B2 | | 12/2011 | Maier et al. |
| 8,182,433 | B2 | | 5/2012 | Leo et al. |
| 8,500,730 | B2 | | 8/2013 | Lee et al. |
| 8,628,520 | B2 | | 1/2014 | Sharareh et al. |
| 8,670,813 | B2 | * | 3/2014 | Tang .................... A61B 5/0071 600/341 |
| 8,712,550 | B2 | * | 4/2014 | Grunewald ......... A61B 18/1492 600/381 |
| 8,842,953 | B2 | | 9/2014 | Mihajlovic et al. |
| 9,526,426 | B1 | * | 12/2016 | Lim ..................... A61B 5/0075 |
| 2006/0229515 | A1 | | 10/2006 | Sharareh et al. |
| 2008/0125634 | A1 | | 5/2008 | Ryan et al. |
| 2008/0287942 | A1 | | 11/2008 | Amundson |
| 2009/0234220 | A1 | * | 9/2009 | Maschke ................ A61B 5/411 600/411 |
| 2009/0234445 | A1 | * | 9/2009 | Maschke ............. A61B 5/0066 623/2.11 |
| 2010/0063492 | A1 | * | 3/2010 | Kahlert ................ A61B 18/24 606/13 |
| 2010/0113906 | A1 | | 5/2010 | Marple et al. |
| 2010/0113919 | A1 | * | 5/2010 | Maschke .............. A61B 17/221 600/424 |
| 2010/0241147 | A1 | * | 9/2010 | Maschke .............. A61B 5/0084 606/159 |
| 2010/0317974 | A1 | | 12/2010 | Alfano et al. |
| 2011/0028837 | A1 | * | 2/2011 | Byrd .................... A61B 5/0071 600/433 |
| 2011/0190760 | A1 | | 8/2011 | Niver et al. |
| 2013/0204134 | A1 | | 8/2013 | Harks et al. |
| 2014/0005553 | A1 | * | 1/2014 | Ryan .................... A61B 5/0062 600/473 |
| 2014/0117256 | A1 | | 5/2014 | Mueller |
| 2014/0343384 | A1 | | 11/2014 | Floyd |

OTHER PUBLICATIONS

Atherton D et al., Clinical Anatomy, Jul. 2012, pp. 628-633 vol. 25 No. 5 (see p. 629-631) Wiley USA.
Barton J. pp. 337-338, Optical-Thermal Response of Laser Irradiated Tissue, 2nd ed., A. J. Welch, M.J.C. van Gemert (eds.), Springer, Netherlands, 2011 (see p. 337-338).
Bays R et al., Proceedings of the SPIE, Nov. 1991, pp. 397-408, vol. 1525, (seee p. 401-407) Soc. Optics and Photonics, USA.
Beauvoit B et al., Biophysical Journal, Dec. 1994, pp. 2501-2510, vol. 67 (see p. 2503-2509).
Chin LCL et al., pp. 678-688, Optical-Thermal Response of Laser-Irradiated Tissue, 2nd ed.,, A.J. Welch, M.J.C. van Gemert (eds.).
Clark III C et al., Journal of Biomedical Optics, Feb. 2011, pp. 020504-1 to 020504-3, vol. 16 No. 2 (see p. 020504-1 to 020504-3) (SPIE).
Cui W et al., Proceedings of the SPIE, May 1991; pp. 180-191, vol. 1431, (see p. 180-191) Soc. Optics and Photonics USA.
Davis M et al., Journal of the American College of Cardiology, Jul. 2013, pp. 231-241, vol. 62, No. 3 (see p. 231-241).
Erdemir, A. et al., Journal of Biomechanics, Mar. 2003, pp. 449-455, vol. 36 No. 3 (see p. 449-455) Am. Soc. Biomechanics US.
Ho S et al., Journal of Cardiovascular Electrophysiology, Nov. 1999, pp. 1525-1533, vol. 10, No. 11 (see p. 1525-1529) Wiley USA.
Kuck et al., Heart Rhythm Journal, Jan. 2012, pp. 18-23, vol. 9 No. 1 (see p. 18-23) Heart Rhythm Soc. USA.
Lindbergh T "Qunatitative Diffuse Reflectance Spectroscopy" 2009 (see p. 62).
Melby SJ et al., Heart Rhythm Journal, Sep. 2008, pp. 1296-1301, vol. 5, No. 9 (see p. 4-6) Heart Rhythm Soc. USA.
Ouyang F et al., Circulation, Jan. 2005, pp. 127-135, vol. 111, No. 2 (see p. 129-135) American Heart Assoc. US.
Pearce JA., Proceedings of the SPIE, Feb. 2009, pp. 718104-1 to 718104-15, vol. 7181 (see p. 718104-1 to 718104-6) Soc. Optics and Photonics, US.
Ranjan R et al., Circulation: Arrhythmia and Electrophysiology, Jun. 2011, pp. 279-286, vol. 4, No. 3 (see p. 282-285) American Heart Assoc. US.
Thomsen S et al., Proceedings of the SPIE, Jun. 1990, pp. 2-11 vol. 1202 (see p. 2-11) Soc. Optics and Photonics, USA.
Yun Sh et al., Optics Express, Jun. 2004, pp. 2977 to 2998, vol. 12 No. 13 (see p. 2978) The Optical Soc. US.

* cited by examiner

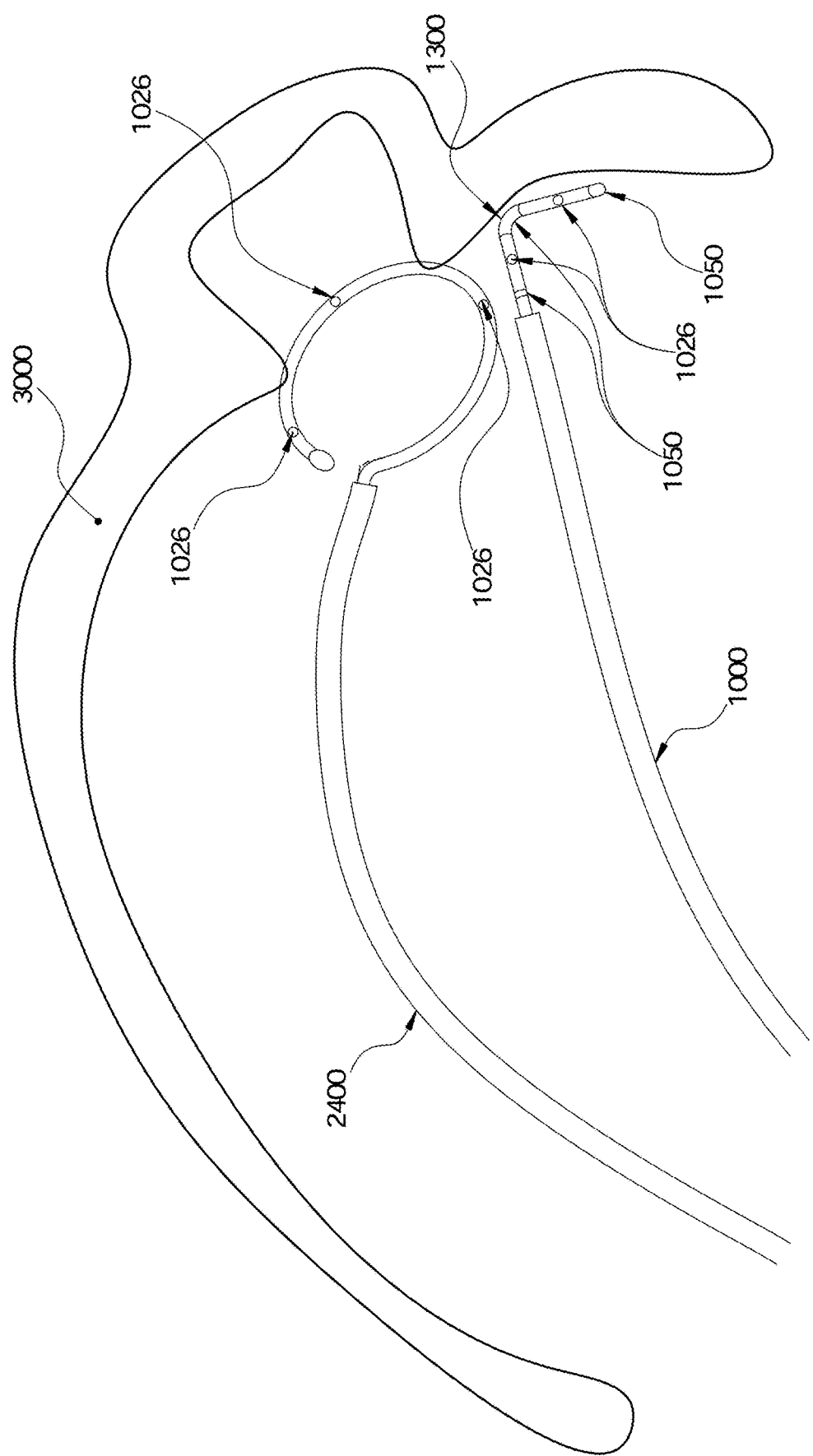

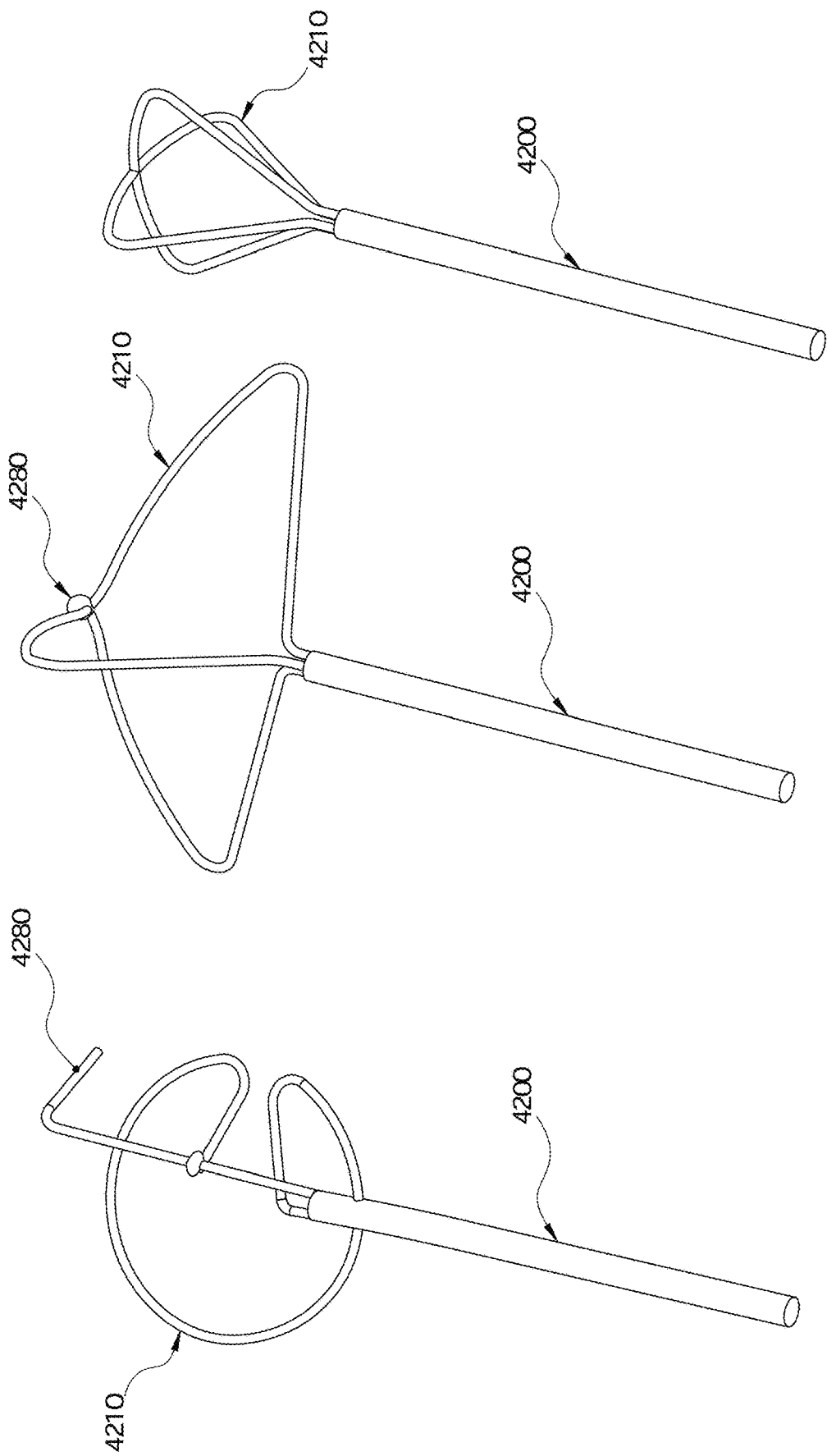

APPARATUS AND METHOD FOR ASSESSING TISSUE TREATMENT

CROSS REFERENCE TO RELATED APPLICATIONS

This application claims the benefit of priority to U.S. patent application Ser. No. 13/945,749, filed Jul. 18, 2013, and to its parent, U.S. Provisional Application No. 61/673,025 filed Jul. 18, 2012, the entire disclosures of which are hereby incorporated by reference.

BACKGROUND OF THE INVENTION

Field of the Invention

The invention relates to a tissue monitoring apparatus, a tissue monitoring method and an ablation lesion monitoring, measuring, and controlling algorithm incorporating diffuse reflectance spectroscopy (DRS) and/or Arrhenius model thermal denaturation kinetics for determining the characteristics of the lesion or the tissue, especially for identifying the transmurality of the ablation lesion. The invention pertains to a device for and method of real time monitoring of lesion formation as ablation is being carried out.

Background Art

Standard ablation catheters in a cardiac space are typically inherently unstable in operation. Methods incorporating the collection of optical spectra are difficult or flawed due to catheter motion and inconsistent contact pressure. Any method incorporating diffuse reflectance spectroscopy (DRS) in a catheter would suffer from these issues. Furthermore, DRS deployed with a standard offset between illuminating and collecting fibers will only penetrate tissue to small penetration depths. Standard catheters cannot achieve a sufficient spatial offset between illuminating and receiving optic fibers due to the limited length of the distal tip of the catheter that is in contact with the heart and therefore cannot exploit a sufficient spatial offset to achieve greater penetration depths.

In ablation of cardiac tissue, the "first hit" (first ablation attempt) is the most important. Therefore applying energy in the correct dosage and for the correct duration the first time is critical to achieving transmurality. Transmurality is critical to a successful outcome.

Insufficient energy and duration will lead to ineffective lesions which result in local tissue swelling and edema which will prevent further effective completion of the lesion at the same location. Checking for lesion characteristics after the first ablation is therefore ineffective. On the other hand, applying too much energy for too long can lead to collateral damage like coagulum formation and damage to surrounding structures.

Including for these reasons, there is a 40% recurrence rate with current ablation technology. One of the primary failure mechanisms is when the lesions are not transmural, that is they do not penetrate the entire way through the tissue and the errant electrical signals can still pass. On the other hand, applying too much energy creates collateral damage to the heart. Thus, the precise application of the right amount of energy is one key to a successful ablation. Unfortunately, it is also very hard to measure, and even worse, the doctor has to get it right the first time.

It has been shown that the recurrence is typically at the deepest tissue layer (Kowalski et al). Thus, it is key that the physician be able to track the lesion formation at deeper tissue levels. When the lesion is formed by the application of RF energy through an electrode, for example, the lesion first forms closest to the electrode. The lesion only later extends to the depths of the tissue. Thus, it is tracking when the lesion reaches the far side of the tissue that is key. This is where the prior art fails. In particular the prior art is unable to provide a catheter that can examine deep within the tissue.

What is therefore needed is a device and method to allow monitoring of the ablation lesion as it is being formed. What is further needed is the ability to adjust power and duration settings according to predetermined optimum levels for achieving transmurality and for preventing collateral damage.

Systems which attempt to measure ablation lesions are known in the art. Certain of these systems rely on optical data. However, quantifying optical sensing data in a beating heart is challenging. There is substantial movement of the catheter. The translation of the catheter can be as much as 1 cm within the timeframe of a single heartbeat. This movement can lead to significant error in spectrophotometer readings and even ultrasound images.

Harks et al., (WO 2012/049621 A1), hereinafter "Harks," incorporates an optical fiber within a standard ablation catheter. This catheter is subject to cardiac motion—leading to significant errors in spectrophotometer readings. The catheter is also subject to different contact pressures which can lead to significant errors in spectrophotometer readings. Furthermore, in moving catheters around the cardiac atria there is a wide variation in the amount of pressure applied to the tissue.

Kuck et.al; A novel radiofrequency ablation catheter using contact force sensing: Toccata study. Heart Rhythm 2012 Jan. 9(1): 18-23 hereinafter "Kuck," shows that there is a large inter-individual and intra-individual variability in ablation catheter contact pressure within the left atrium. Even within the various contact levels made by a single individual clinician during a single procedure, there is a wide variability in contact pressure as the catheter is moved from point to point in the heart. This contact pressure can differ by as much as up to 40 g as the ablation catheter is moved around just the pulmonary veins. In addition, depending in the individual clinician performing the ablation, a large variation in contact force of up to 60 g is possible Irrespective of the source, variability in pressure against tissues can influence measurement of optical sensing data. Variations in pressure on tissue can lead to variations in scattering and absorbance coefficients by as much as up to 25% due to extrusion of water from tissue.

Accordingly, the prior art also lacks a stable platform providing a stable contact pressure for measuring the lesion.

In addition, with past ablation systems such as those used for atrial fibrillation and ventricular tachycardia, there is no method of checking for transmurality. It is up to the operator to decide (or guess) when the lesion is transmural. The result is a significant variation in power delivery and duration of power delivery between different operators. As a result of this, there is a significant recurrence rate of arrhythmias, between 30 to 50 percent for atrial fibrillation. For ventricular tachycardia, the recurrence rate is even higher because ventricular tissue is thicker and so it is harder to achieve transmurality.

Studies have shown that when inpatients come back with recurrence of atrial fibrillation, the pulmonary veins typically have electrically reconnected, proving the inability of current ablation systems to achieve transmurality.

While the atrial tissue may be as thick as 5 mm, histology studies have shown that a rim of unablated tissue as little as 1.4 mm can lead to reconnection of pulmonary veins and lead to recurrence of atrial fibrillation.

In ablation catheters adapted for renal denervation where the sympathetic nerves on the surface of the renal artery are the targets for ablation, there is currently no ablation endpoint. As such, the operator is not able to discern when the nerves have been ablated. As such there have been reports of thrombus formation and even dissection of the renal artery, due perhaps to delivering too much power for too long.

Accordingly, It would be desirable to provide a system that is configured to interrogate deeper layers of tissue to select out the layer of tissue for ablation and to observe for transmurality with NIR spectroscopy and that can provide a constant contact force and also reduce the effect of the beating motion

BRIEF SUMMARY OF THE INVENTION

In one embodiment, the invention includes s system for monitoring tissue including a catheter having an elongated body member with a proximal end and a distal end, a biasing element in the distal end, the biasing element configured to bias the distal end into contact with a first tissue portion, an optical emitting element, the optical emitting element oriented to emit optical radiation into the first tissue portion, an optical receiving element oriented to collect optical radiation, the optical radiation indicating characteristics of the first tissue portion. The optical receiving element and the optical emitting element are arranged to be spatially offset along a first longitudinal axis of the distal end, and along the face of the first tissue portion. The system also includes a workstation that includes an optical radiation analysis module configured to process the optical radiation collected by the optical receiving element using spatially offset diffuse reflectance spectroscopy.

In another embodiment, the invention includes a catheter that includes a diagnostic assembly with a longitudinal axis that lies alongside a first tissue portion. The diagnostic assembly includes an optical emitting element configured to emit optical radiation into the first tissue portion, an optical receiving element configured to collect optical radiation indicating characteristics of the first tissue portion. The optical receiving element and the optical emitting element are arranged to be spatially offset along the longitudinal axis. The invention includes a processing element configured to process the optical radiation using spatially offset diffuse reflectance spectroscopy.

The catheter may include one or more apertures wherein the optical emitting and receiving elements are configured to emit and receive optical radiation through the apertures.

In one embodiment the catheter's distal portion includes a basket assembly including a plurality of radially expanding splines adapted to position the respective spline adjacent a tissue. One or more splines may include diagnostic assemblies. Additional splines may include additional emitting and receiving elements.

The catheter may include a detection optical fiber displacement actuator 1610 configured to adjust the spatial offset between the optical receiving element and the optical emitting element along the first longitudinal axis such that the spatial offset between the optical receiving element and the optical emitting element is adjustable. In some embodiments the catheter includes an electrode.

In some embodiments the processing element is configured to generate an optical spectra of the optical radiation collected by the optical receiving element. The processing element may do so by comparing the generated optical spectra of the optical radiation collected by the optical receiving element to a reference optical spectra for fat, nerve, muscle, or collagen. The processing element can be configured to determine that adjacent tissue is at least one of the following tissue types: fat, nerve, muscle, or collagen based on the comparison between the generated optical spectra and the reference optical spectra. The processing element can use Near Infrared, NIR, Raman, Fluorescence spectroscopy, birefringence, and OCT to collect depth data, which is the depth of the muscle tissue at a particular point.

In some embodiments the processing element is configured to compare the generated optical spectra of the optical radiation collected by the optical receiving element to a reference optical spectra for tissue fluid. In some embodiments the processing element is configured to automatically calculate the rate of thermal denaturation of the tissue adjacent to the first radially expanding spline. In some embodiments the processing element is configured to extract a rate constant for the rate of thermal denaturation when the tissue adjacent to the first radially expanding spline is sixty three percent denatured. In some embodiments the spatial offset between the optical receiving element and the optical emitting element is at least 10 mm.

In some embodiments the catheter apparatus is connected to an optical radiation source configured to provide optical radiation to the first and the second optical illuminating elements such that the first and the second optically illuminating elements substantially simultaneously emit optical radiation.

In another embodiment the invention comprises a system for monitoring tissue. The invention includes a display, a catheter, the catheter having an elongated body member having a proximal end and a distal end adapted to contact a first tissue portion, and including an optical emitting element, the optical emitting element oriented to emit optical radiation into the first tissue portion, an optical receiving element oriented to collect optical radiation, the optical radiation indicating characteristics of the first tissue portion; and the optical receiving element and the optical emitting element are arranged to be spatially offset along the first longitudinal axis of the first radially expanding spline, and along the face of the first tissue portion. The invention includes a workstation comprising an optical radiation analysis module configured to process the optical radiation collected by the optical receiving element using spatially offset diffuse reflectance spectroscopy.

BRIEF DESCRIPTION OF THE DRAWINGS

FIG. 19 shows a cross section of the catheters in a multiple catheter embodiment;

FIG. 20c shows a cross section of one catheter embodiment of the present invention;

FIG. 20d shows a cross section of one catheter embodiment of the present invention;

FIG. 20e shows a cross section of one catheter embodiment of the present invention;

DETAILED DESCRIPTION OF THE PREFERRED EMBODIMENTS

Figure 1:
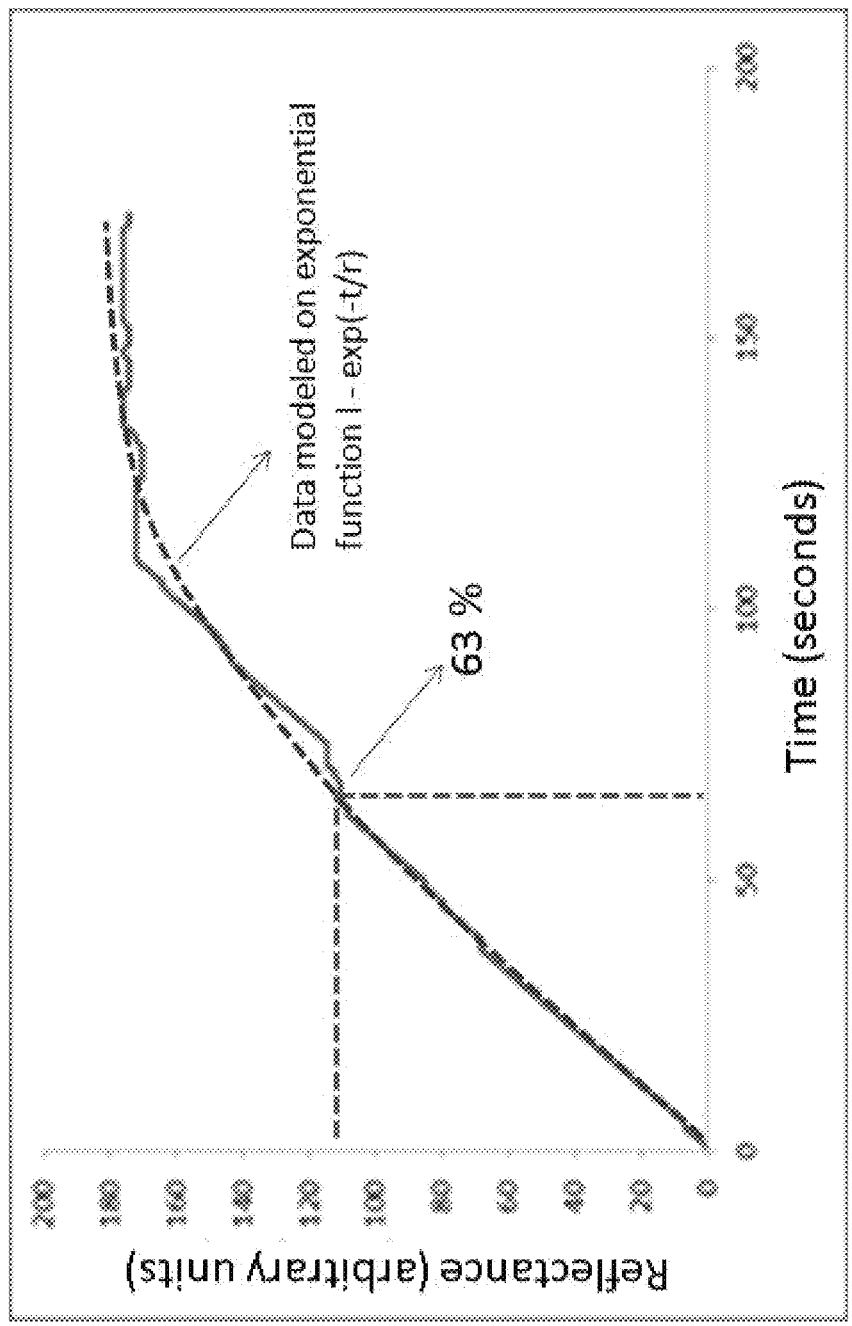
FIG. 1 is an exemplary Arrhenius equation.

In general, the invention comprises a medical procedure and corresponding medical devices for generating optical sensing data indicative of an optical property of a tissue. More specifically, the invention relates to a tissue monitoring apparatus, a tissue monitoring method and an ablation lesion monitoring, measuring, and controlling algorithm incorporating diffuse reflectance spectroscopy (DRS) and/or Arrhenius model thermal denaturation kinetics for determining the characteristics of the lesion, nerves, or the tissue, especially for identifying the completion of the ablation lesion. The invention pertains to a device for and method of real time monitoring of lesion formation as ablation is being carried out.

Setting Appropriate End Points for Ablation

Atrial Fibrillation Ablation

As tissue is undergoing heat denaturation, for example, by ablation, the tissue's optical properties change. Beauvoit et al. reported that the mitochondrial compartment is the primary cause of light scattering. Thomsen et al., observed disruption of mitochondria into coarse granules, and discerned small aggregates resulting from denaturation of fibrillar contractile proteins and other cytoplasmic constituents. Based on their observations, Thomsen proposed that these thermally induced morphological changes are the physical cause of the increased rat myocardial tissue scattering observed with thermal coagulation.

Optical properties used to monitor the progress of ablation can be scattering, absorption or reflectance. Reflectance can be an effective parameter to monitor the progress of ablation. Reflectance, however, is a composite of the changes in absorption and scattering that is occurring as the ablation process continues. Monitoring the progress of ablation can also be confounded by the differing absorption properties of the different layers of tissues that are present in the tissue to be ablated. Furthermore, as the ablation process continues blood leakage, tissue edema and tissue shrinkage can lead to dynamic changes in scattering and absorption properties which can confound the monitoring process. For example, tissue swelling and edema can occur after 500 seconds. One must therefore account for these aforementioned factors in order to be able to use reflectance to monitor the ablation process accurately.

By monitoring changes in these scattering optical properties, one can monitor the progress of the ablation. While certain catheters have attempted to monitor a tissue's surface, this is of limited, at best, value as an ablation lesion must be transmural to be effective. The prior art does not identify a catheter that can examine deep within the tissue, and thus is unable to provide a catheter that can monitor for the crucial transmural lesion.

The present invention solves this issue by providing a system that is engineered to allow the use of spatially offset diffuse reflectance spectroscopy. The depth of the muscle layer in the left atrium can range up to 5 mm deep. Thus, in order to ensure a transmural lesion is present, an optical sensing technology must be able to interrogate at least 5 mm depth.

In diffuse reflectance spectroscopy the emitting and receiving elements are placed at a particular distance from each other. Unlike the prior art, in applicant's system the visualization elements are laid along the tissue just like an electrode is, e.g., the emitting element at a first point, then the ablation electrode, and then the receiving element. In the case of an RF ablation electrode, all three elements are preferrably in contact with or close to the tissue.

Figure 10:
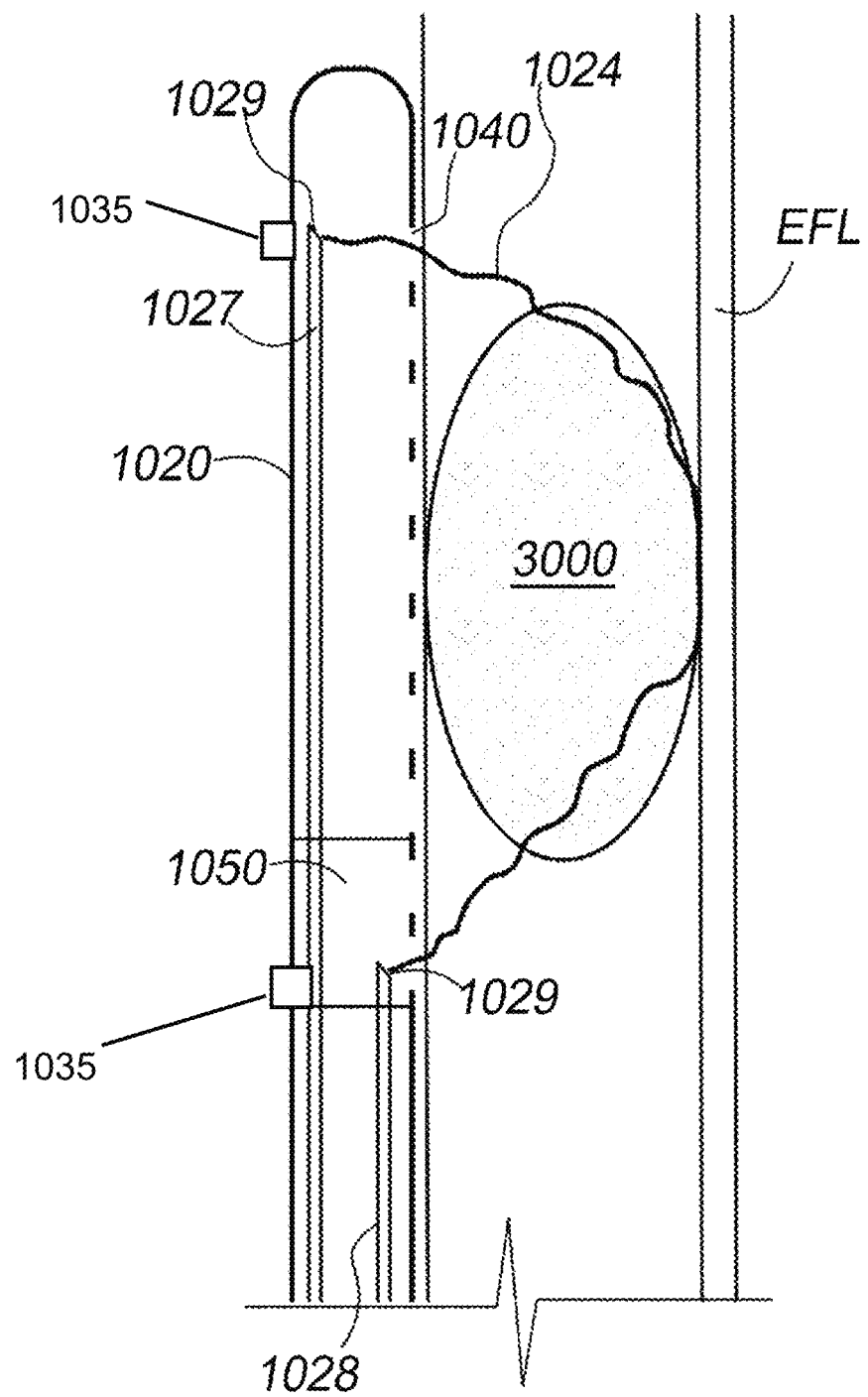
FIG. 10 shows a cross section of a hollow tube of a catheter or spline, and optic fibers therein.

In its most basic format, with reference to FIG. 10, the present invention comprises a probe 1000, such as a catheter, guidewire, introducer, spline, catheter portion, or the like with an emitting optical fiber 1028 and a receiving optical fiber 1027. The two fiber end points are spatially offset along a longitudinal axis of the probe 1000, and preferably alongside the axis of the tissue's surface. By "along the tissue" applicants mean that if one were to draw a line or an axis between the fibers, that line would lie substantially along the tissue's surface (the tissue is not likely to be perfectly flat or linear). Optical radiation, e.g., near infrared light, is emitted from fiber 1028 and received by fiber 1027. As the ablation proceeds, the tissue changes, and accordingly the radiation received by fiber 1027 changes. By monitoring changes in these optical properties, one can monitor the progress of the ablation. The location of that measurement will depend on the spatial relationship between the two fibers. Applicants have found that the longer the offset along the length of the tissue, the deeper the measurement. Thus, the fibers may have a fixed or variable spatial offset along the tissue.

The optic fibers may be attached in a number of ways. First, the optic fibers may be in a lumen in a catheter, spline, or strut. Second, the optic fibers may be outside the catheter, spline, or strut, but attached with glue, friction, or a heat shrink. Collars may periodically attach the fibers to the device. The fiber may be attached by a glue or adhesive, e.g., an epoxy or by welding. Likewise, electrodes or other sensors may acts as fasteners or crimps to hold down the optic fibers.

Advantageously, the reflectance signal may be monitored to measure the progress of the ablation. As mentioned, however, reflectance is a composite of the changes in absorption and scattering that is occurring as the ablation process continues and thus these changes in absorption and scattering must be eliminated.

The reflectance signal is invariant to increased absorption at 800 nm. We can therefore probe ablated tissue based on measuring the ratio between the reflectance signal at two wavelengths, for example one wavelength around the wavelength of interest (ranging from 400-2500 nm) and one around 800 nm. Normalized reflectance values are therefore obtained by obtaining a ratio of the reflectance at a particular wavelength to the reflectance at 800 nm. This ratio will allow the cancelling out of absorbance. Normalized reflectance will then be used to monitor the ablation process in real time by tracking the rate of change of the normalized reflectance.

As ablation is being carried out, conductive heating and thermal diffusion through tissue leads to temperature elevation and the tissue temperature rises. This leads to the changes in the size and/or location of the optical scattering centers like the mitochondria due to disruption of mitochondria into coarse granules, and denaturation of fibrillary contractile proteins and other cytoplasmic constituents resulting in the formation of small aggregates that leads to an increase in the normalized reflectance. When ablation is started, there may be a lag phase of between 1 to 4 seconds (which may represent the time it takes for conductive heating and thermal diffusion through tissue) before there is a rise in the normalized reflectance. A steady rise in normalized reflectance is followed by a plateau where there is no change in the normalized reflectance, at which point the tissue is considered 100% denatured at the depth being interrogated. Changes in normalized reflectance during the early time course of the ablation are fitted to the curve to the exponential function I−exp(−t/r).

By modeling the above reaction on the Arrhenius equation for thermal denaturation, one can obtain the rate constant for the reaction which is equivalent to the slope of the curve at the point where 63% of the tissue is denatured. Referring to FIG. 1, the reaction defined by the exponential function I−exp(−t/r), r is the rate constant of the denaturation reaction and is the value of the normalized reflectance when 63 percent of the tissue is denatured.

The Arrhenius equation for thermal damage is given by:

$$\Omega(\tau) = \int_0^\tau A e^{\left[\frac{-E_a}{RT(t)}\right]} dt$$

Where omega is the damage integral and is the logarithm of the ratio of the original concentration of native tissue to the remaining native tissue state at time torque, A is a frequency factor ($s^{-1}$), the total heating time (s), Ea an activation energy barrier (J·$mole^{-1}$), R the universal gas constant, 8.3143 (J·$mole^{-1}K^{-1}$) and T the absolute temperature (K). The damage integral is therefore an indication of the percentage of proteins that have undergone denaturation. The damage integral is given by the rate of change of normalized reflectance. There is a critical temperature for which the damage integral is 1, that is 100% of tissue would have undergone denaturation for a given duration. For myocardial tissue, this critical temperature is 60 degrees Celsius. Accordingly, the Arrhenius equation predicts that for a given temperature 100% of tissue will be denatured for a given duration of exposure. For a series of lesions created at different temperatures but resulting in equivalent damage, a linear fit would yield AE/R as the slope, and −ln(A) as the intercept.

This Arrhenius model prediction for tissue damage may be then compared to histological results, for example, nitroblue tetrazolium staining of ablated tissue as a marker of transmurality of the lesion, where 100% denaturation is equivalent to 100% transmurality Ex vivo and in vivo experiments are performed where the rate constant associated with a range of tissue temperature from 45 to 75 degrees Celsius (as determined by a thermocouple embedded in the tissue) and 100% transmurality (as determined by histology using NBT to assess for non-viability of tissue) will be determined and stored in the memory of the system.

The optimal rate constant associated with a tissue temperature of 60 degrees Celsius which will ensure 100% transmurality (as determined with histology using NBT to assess for non-viability of tissue) within an ablation time of between 10 to 60 seconds will be determined from the ex vivo and in vitro experiments and will be stored in the memory of the system. At the point where 100% tissue denaturation occurs, there is no further change in the reflectance properties of tissue observable as a plateau (the rate of change of normalized reflectance is zero). Therefore, by monitoring ablation process in real time, one can determine precisely the moment the tissue is denatured.

In some embodiments the ablation continues until the tissue is 100% denatured. In other embodiments the ablation energy is discontinued when the tissue is partially ablated, e.g., 63% or 80% transmural, or in another embodiment the ablation is discontinued when the deepest tissue layer to be ablated is 63% or 80% denatured. In such embodiments the tissue may continue to ablate due to residual heat present in the tissue, effectively completing the lesion.

The point at which 100% tissue denaturation occurs leading to the plateau is time sensitive. There is a late phase after about 300 to 500 seconds where edema, blood leakage and tissue shrinkage will occur which can lead to changes in the normalized reflectance. In one embodiment, immediately at the time point where the plateau is reached, the emitting and receiving optic fibers are scanned rotationally by a galvanometer from side to side, to determine the area of the ablated region at the surface. For determining the optical spectra, the optical sensor can illuminate the inner wall of the heart with light having different wavelengths, wherein the optical spectra are generated by using the spectrometer. Alternatively, the optical sensor can be adapted to illuminate the inner wall of the heart with different wavelengths temporally consecutively such that the optical fibers for receiving light from the inner wall of the heart receive light from substantially only one wavelength.

The wavelength of interest may range from 400 nm to 2500 nm. For example, a wavelength of 2060 nm wherein a shift to a lower wavelength of 2056 nm corresponding to protein unfolding and protein denaturation from thermal energy application can be selected to discriminate between ablated and non-ablated muscle tissue. The receiving optic fiber is rotated until the spectra, e.g., the NIR spectra here, for non-ablated tissue is discerned whereby the angle of rotation with the distance travelled gives an indication of the area ablated. Information obtained in the foregoing steps can be integrated with depth information to give a 3D representation of volume of ablated tissue, and is compared against histological and also spectroscopic assessments of volume of NBT dye staining.

By incorporating the measurement of the changes in normalized reflectance with respect to time into Arrhenius equation for thermal damage, the present invention offers the advantage that the slope of the reflectance curve changes as the fat layer is reached. In some cases a change in the slope of the reflectance curve (or possibly the plateau where the rate of change of normalized reflectance is zero) can be registered sensitively at an earlier time frame/window (20 to 80 seconds) before edema, blood leakage and tissue shrinkage sets in (300 to 500 seconds) and therefore avoids the confounding influence of these factors on tissue optical properties.

Ex vivo and in vivo experiments determine the lag phase r which is the rate constant (or slope) for that reaction at that a particular temperature and the time to the plateau which will ensure 100% transmurality as based on NBT staining of tissue. Accordingly, there is an optimal lag phase, slope and time to plateau to get complete lesions before tissue edema sets in and prevents the measurement or achievement of an effective ablation lesion. Stored rate constants of various energy and power settings (and the corresponding temperature) correlating with different times to plateaus, the lag phase associated with different pathological assessments showing different degrees of transmurality will be stored in the memory of the system and used to guide ablation.

In cases where the operator is using too low of a power setting (and thus edema may set in before the lesion may be transmural), there will be a significant deviation from the Arrhenius model and the algorithm can operate to shut off the power to prevent the operator from delivering an ineffective lesion or the algorithm can increase the power to get the operator back onto the curve (the right rate constant) and back onto the right track. Alternatively the system can advise the operator to change settings and allow the operator to do so.

The technology can also be adapted for sensing tissue damage caused by other energy forms, for example, cryoablation. In cryoablation, denaturation of tissue is heralded by the formation of intracellular ice crystals.

There is a difference in the absorption spectra of ice and water around 1600 nm so that an ice/water discrimination algorithm is used. The transformation from intracellular fluid to ice crystals can be monitored with NIR spectroscopy at between 1000 to 2050 nm wavelength. Furthermore, while the crystals do not characteristically destroy cell membranes, they compress and deform nuclei and cytoplasmic components, which will lead to a change in the reflectance and can be monitored in real time.

Based on the data accumulated in ex vivo and in vivo experiments, the invention's incorporated algorithm will be able to take the operator's power settings, lag phase and rate constant, compare it against the data in stored memory and allow the operator to calculate the percentage of denatured tissue in real time; i.e., 10%, 20% 50% etc., and tell the operator when he is done. This can be displayed on a user interface display unit. Because the measurements of normalized reflectance are performed as a function of time and depth, an M mode image can be generated that will provide a visualization of the thermal process. Using data from ex vivo and in vivo experiments, the depth information obtained from the spatially offset diffuse reflectance is compared against the histological data. This data is then integrated with data about the area of the ablation lesion at the surface to generate a 3D representation of the lesion which can be generated in real time.

In some embodiments, the system is also adapted to translate the receiving optic fiber as the ablation process is occurring wherein the initial position of the receiving optic fiber before ablation is carried out is located close to the illuminating fiber. As the ablation starts, the receiving optic fiber is translated away from the illuminating optic fiber or vice versa. The distance between the illuminating and receiving optic fiber corresponds to the depth at which the photons have traveled and represents the depth of the muscle layer the optical sensor is interrogating.

In spatially offset diffuse reflectance spectroscopy (SODRS) the path of photon travel through tissue is "banana shaped" (See FIG. 10, path 1024). Thus, the depth of tissue interrogated will be approximately half the distance of the spatial offset. The geometry of standard ablation catheters does not permit the wide spatial offset between illuminating and receiving optic fibers positioned at the distal tip that is required to truly analyze. Typically only between 3 to 4 mm of the distal tip of the catheter is in contact with the muscle tissue. It is difficult to ensure a constant end-on or side-on contact of standard ablation catheters with the tissue surface. Furthermore, prior art systems using optical fibers for various purposes typically have a spatial offset of 1.7 mm or less and as a result, if adapted for the use of SODRS are only interrogating the superficial tissue layers of 0.4 to 0.8 mm.

The system is programmed to track the duration of the ablation process (according to the rate constant and the time to the plateau data from in vivo and ex vivo experiments,) in the tissue for between 20-60 seconds until the slope of the reflectance curve changes (or a plateau is obtained), signifying that the muscle layer is denatured at this depth. By performing these measurements as a function of time and depth, M-mode images that provide a visualization of the thermal therapy process can be generated. The depth-localized intensity of the signal magnitude fluctuations is mapped according to a color bar. The maximum amplitude of the reflectance signal is plotted against time in an "M-mode image." The M-mode image is formed by mapping the reflectance signals to the indicated color space.

Determination of the Scattering and Absorption Coefficients from Spatially Offset Diffuse Reflectance Spectroscopy The present invention is further adapted to determine the kind of tissue or the composition of tissue. Optical spectra assigned to different types of tissues, for example, fat, nerve, muscle, collagen, water are stored in the memory wherein the present invention is adapted to determine the respective kind of tissue or the composition of tissue under examination during a procedure by comparing the stored optical spectra with examined optical spectra. For determining the optical spectra, the optical sensor can illuminate the inner wall of the heart with light having different wavelengths, wherein the optical spectra are generated by using the spectrometer.

Alternatively, as described in the foregoing exemplary embodiment above under the section "Setting appropriate end points for ablation", the optical sensor can be adapted to illuminate the inner wall of the heart with different wavelengths temporally consecutively such that the optical fibers for receiving light from the inner wall of the heart receive light from substantially only one wavelength. In this situation, a spectrometer may not be needed but may be replaced by a photodetector that is sensitive to the respective wavelength(s). Therefore, the output of the optical fibers, which have received the light from the inner wall of the heart, can be detected by a photodiode for generating a detector signal and the detector signal can be processed in accordance with an algorithm as will be described below. In an alternative embodiment the receiving fiber can be entirely replaced by a photo detector at the desired location in the catheter.

The present invention uses spatially offset diffuse reflectance spectroscopy to collect reflectance spectra. It is advantageous to extract scattering and absorption coefficients from reflectance data obtained by SODRS. In order to extract absorption and scattering properties from reflectance measurements, spatially resolved intensities need to be obtained.

Embodiments according to the present invention are adapted to measure the diffusely reflected light intensity of the tissue at different distances from the small illuminated surface spot. For tissue, the separation distances are in the range of between 2 to 20 mm. Therefore, the optical properties can be derived from reflectance profiles measured at 10 source detector separated locations. Embodiments according to the present invention use a scanning approach with a side deflected illumination fiber and collection fiber, and in some embodiments one of the fibers be translated axially. Other embodiments may employ a separate fiber at each axial location. The excitation light enters the probe via an optical fiber and is focused on the tissue surface near the end of the probe with the aluminized mirror surface on the polished angled surface of the distal end of the optic fiber. The intensity of the diffusely reflected light at the surface at different distances from the excitation spot is probed by displacing the movable optical fiber along the probe in such a way as to measure the light passing through the apertures, holes, or other optically transparent portions one after the other (counting the number of maxima in the measured diffuse reflectance curve).

In some embodiments this automatically gives the radial distance from the illumination spot along the surface, as the position of each hole is known. The fiber of the detection assembly then guides the light to a photomultiplier, the signal of which is amplified using a lock-in technique. A monochromator is inserted between fiber end and photomultiplier to avoid possibly important contributions from autofluorescence. The logarithm of the observed signal I (arbitrary units) is plotted against distance along the surface between excitation source and probing point. This data is then fitted to an analytic expression, which is based on diffusion theory. From the radial dependence of the diffusely reflected light intensity at the surface of the organ concerned, the tissue optical parameters may be extracted using the Groenhuis model.

The present invention can be adapted to use the algorithm to extract the tissue optical parameters, the scattering and absorption coefficients as disclosed in "Clinical optical dose measurement for PDT: Invasive and non-invasive techniques" by R Bays et al., SPIE Vol. 1525 Future Trends in Biomedical Applications of Lasers (1991), pages 397 to 408.

The present invention, using the algorithm described above can therefore determine the scattering coefficients and the absorption coefficients of different tissue chromophores like fat, water, muscle, collagen and nerves.

The present invention can also be adapted to discriminate differences in optical spectra by making use of a principal components analysis as disclosed in "Partial Least-Squares Methods for Spectral Analyses. 1. Relation to Other Quantitative Calibration Methods and the Extraction of Qualitative Information by David M Haaland et al., Analytical Chemistry, vol. 60, no. 11 pages 1193 to 1202, June 1988, which is herewith incorporated by reference in its entirety. The principal component analysis allows classification of differences in optical spectra and, thus allows discrimination between tissues, in particular, between fat and muscle, between muscle and collagen, between fat and nerves and between ablated and non-ablated tissue.

The present invention can also be adapted to discriminate between areas of heart muscle tissue infiltrated with fibrosis and areas with no fibrosis. In this embodiment, a bigger sized basket (for example 50 mm in diameter) is placed in the left atrium so that the basket approximates the endocardial surface of the left atrium.

Figure 13:
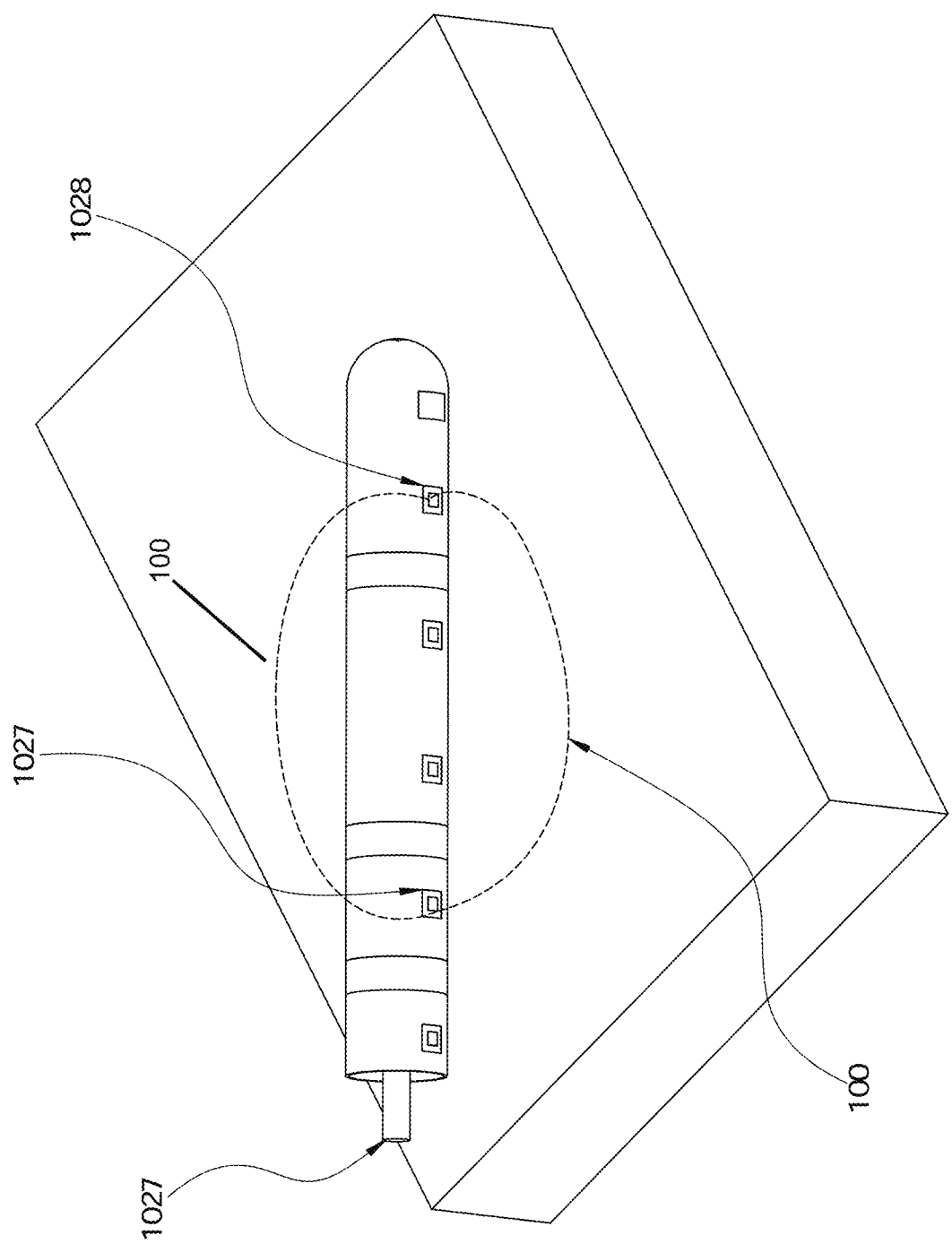
FIG. 13 shows a view of the photon travel paths of one embodiment according to the present invention.

The path of the photon travel from the emitting element to the receiving element should be thought of three dimensionally (FIG. 13). Thus, the emitting element or the receiving element may be rotated to send or receive the photon along any number of paths 100, 100', etc. In some embodiments, the receiving optic fiber is scanned along the length of the spline in an axial direction and also rotationally in a side to side manner. As the receiving optic fiber is scanned along the surface of the tissue, it is able to distinguish for example, between areas of fibrosis (collagen) and muscle, fat and muscle, nerve and fat, muscle and fat. In other embodiments, the emitting fiber is scanned along the length of the spline in an axial direction and also rotationally in a side to side manner. In another embodiment both the emitting and receiving fibers are scanned along a portion of the length of the spline in an axial direction and also rotationally in a side to side manner. Additionally, the invention may utilize multiple fibers that alternate as emitting or receiving fibers to sequentially or simultaneously interrogate different tissue depths and locations.

Figure 14:
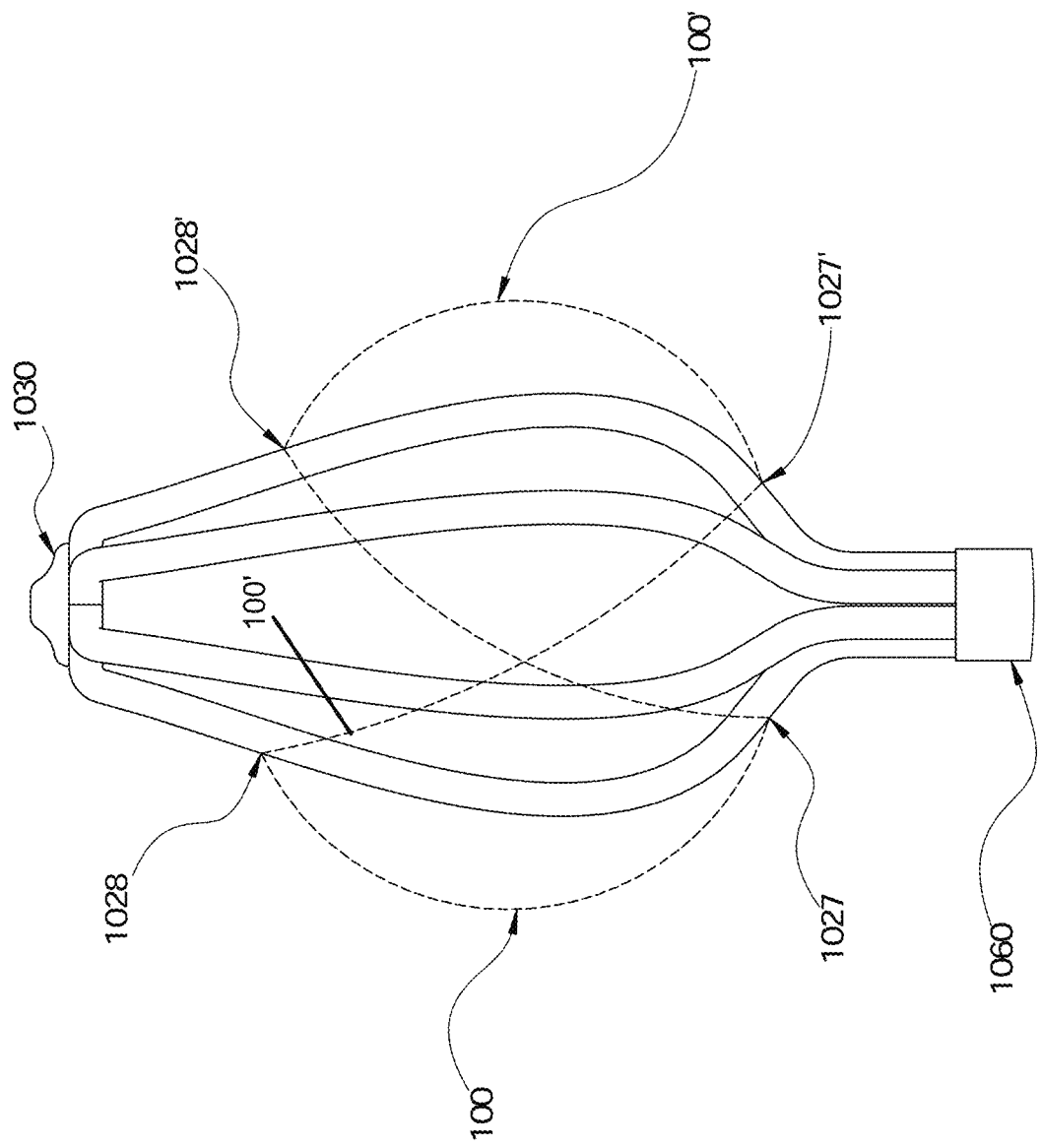
FIG. 14 shows a catheter with a cone shaped basket configuration at the distal end.

Thus, as shown in FIG. 14 there may be multiple emitting fibers 1028, 1028' and multiple receiving fibers 1027, 1027'. 1028 may talk (100, 100') with either or both of 1027 and 1027', and likewise, 1028' may talk with either or both of 1027 and 1027'. Of course, three or more fibers are also contemplated, but two are shown for simplicity.

By allowing movement, rotation or by including multiple fibers, the three dimensional shape of the scan can take any desired shape.

The present invention is adapted to localize the depth of the fibrosis, fat, nerve and muscle with the algorithm described above that is adapted for spatially offset diffuse reflectance spectroscopy. The areas and location of interest, or example fibrosis, fat, and nerve can be tagged with the localization unit that is adapted to provide (x, y and z coordinates) of the area of interest, with a color scale denoting the concentration of fibrosis correlated with intensity of the optical parameter (for example, reflectance, scattering or absorption coefficient).

Before Ablation is Started, the Thickness of the Muscle Tissue Layer to be Ablated May be Determined As mentioned previously, the present invention can be adapted to distinguish between fat and muscle to determine the depth at which ablation should be carried out by comparing an actually measured optical spectrum with stored optical spectra which are assigned to fat or muscle tissue.

In atrial fibrillation ablation, the adventitial fat layer represents the boundary beyond which the ablation should not be carried out, for example to avoid damage to the esophagus which lies beyond the adventitial fat layer of the left atrium.

The present invention can also take advantage of the different electrical conductive and correspondingly related optic properties of fat and muscle to limit the ablation before the fat layer to achieve transmurality and also prevent collateral damage. For example, the slope of the reflectance curve may change as the fat layer is reached. The spectra, e.g., the NIR spectra, for fat tissue and for muscle tissue and for nerves is stored in the memory of the invention. In order to compare an actually measured optical spectrum with stored optical spectra, the present invention is preferentially adapted to use a similarity measure like a correlation or a sum of squared differences.

At the beginning of the ablation procedure (and prior to the ablation), the illumination or emitting optic fiber is fired and the receiving optic fiber is scanned along the tissue to probe the deepest depth of the tissue until it registers the NIR signature of fat. This represents the deepest adventitial layer of fat beyond which the ablation should not proceed. This is also the layer where critical structures like the phrenic nerve, adjacent to the right superior pulmonary vein are located. If the initial scanning process registers the NIR signature of nerve over the location of the right superior pulmonary vein, an alternative site may be targeted for ablation to prevent injury to the phrenic nerve. The depth at which the fatty adventitial layer is recorded at is, for example, 5 mm. The spatial offset is then adjusted until the NIR signature of muscle is recorded. The muscle layer of the left atrium lies superficial to the fatty adventitial layer. So the depth of this muscle layer will be for example 4 mm. Ablation is then carried out. As discussed above, as the ablation is carried out, a change in reflectance occurs. This change in reflectance will be normalized to get a ratio which will cancel out the effects of absorbance. This change in reflectance with respect to time can be fit to an exponential function which is modeled on the Arrhenius equation for thermal denaturation. The Arrhenius equation can predict a 100% transmurality (i.e., denatured tissue) for a particular tissue temperature (for example 60 degrees Celsius) held for a particular duration (for example 20 seconds). This particular set of conditions is associated with a thermal denaturation exponential curve with a rate constant that is given by the slope of the curve whereby 63% of the tissue has been denatured.

Ex vivo and in vitro experiments are performed with a thermocouple embedded into the target tissue to record the tissue temperature during ablation with a series of tissues temperatures recorded for different power settings with the tissues stained with NBT (or TTC) to determine the amount of viable tissue and therefore the extent of transmurality. Thus the exponential curve with the rate constant associated with a tissue temperature of 60 degrees Celsius and 100% transmurality and the duration required to achieve 100% transmurality is stored in the memory of the invention.

During an ablation procedure, an automated algorithm will reference this stored value with the current parameters of the thermal denaturation of ablation process and the power can be adjusted or titrated to approximate the stored value. When the exponential curve reaches a plateau, signifying 100% denaturation, the ablation process is terminated to avoid carrying the ablation process beyond the muscle into the adventitial fat layer, causing collateral damage. By way of a non-limiting example, the following represents a preferred algorithm for atrial fibrillation ablation: Transeptal catheterization→Steerable sheath guided into pulmonary vein→Steerable sheath withdrawn→Basket expands to preformed shape→Basket withdrawn until it abuts tightly against the opening of the pulmonary vein with the radiopaque markers on the electrode signifying the desired position of the electrode at the os→illumination optic fiber is fired→Receiving optic fiber is translated by galvanometer→NIR spectra is compared with NIR spectra of fat stored in memory→Adventitial fat layer identified-→Further scanning and/or rotation of the basket is performed until NIR for nerve is identified→Catheter position adjusted as needed→Ablation is performed→Rate of change of normalized reflectance is followed as an exponential curve and the lag phase, the slope of the curve of the current reaction is compared against the reaction where 100% transmurality was obtained at a temperature of 60 degrees Celsius over a duration of 40 seconds→If the slope is less than the one stored in memory, computer algorithm then commands the energy delivery unit to increase the power until the slope matches the one for the ideal reaction rate stored in memory.

Renal Denervation

Figure 22:
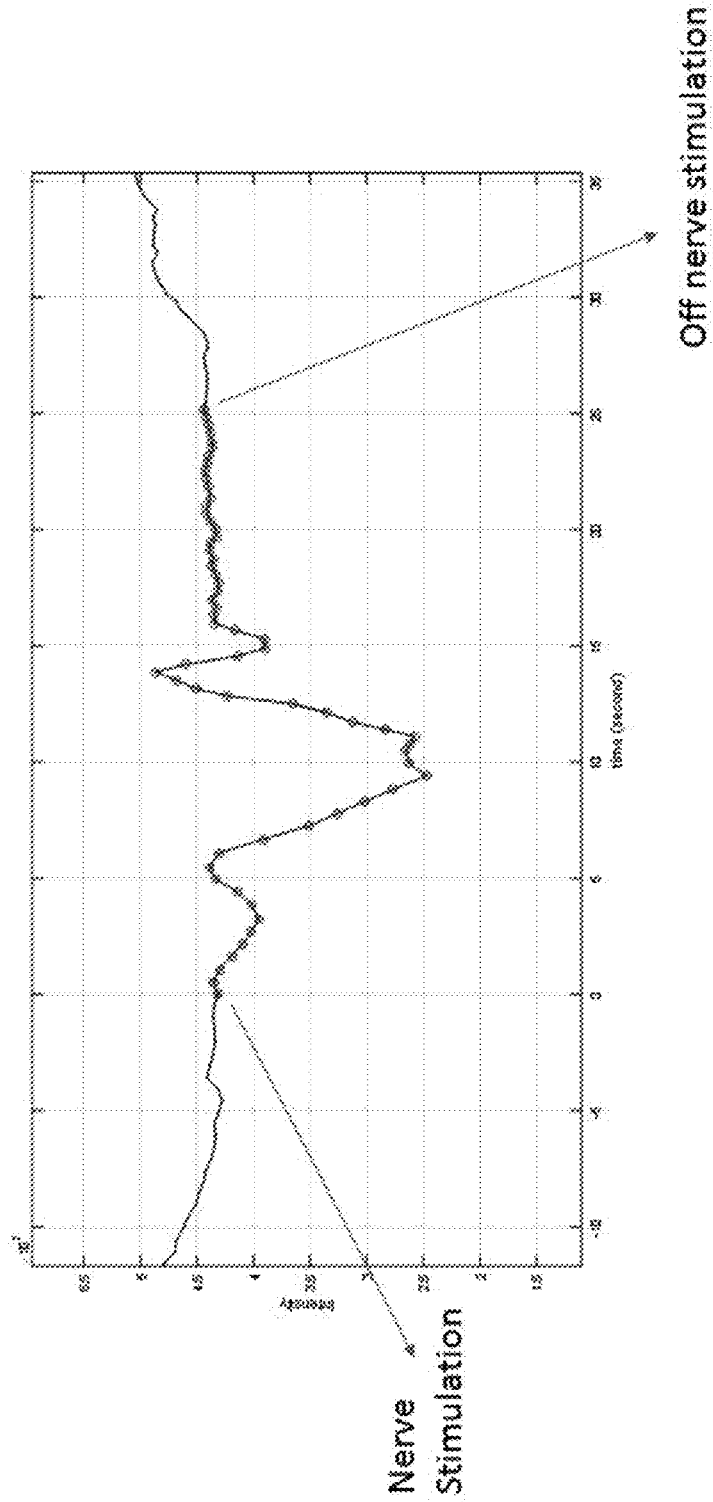
FIG. 22 shows the correlation of NIR scattering with nerve activity.
Figure 23:
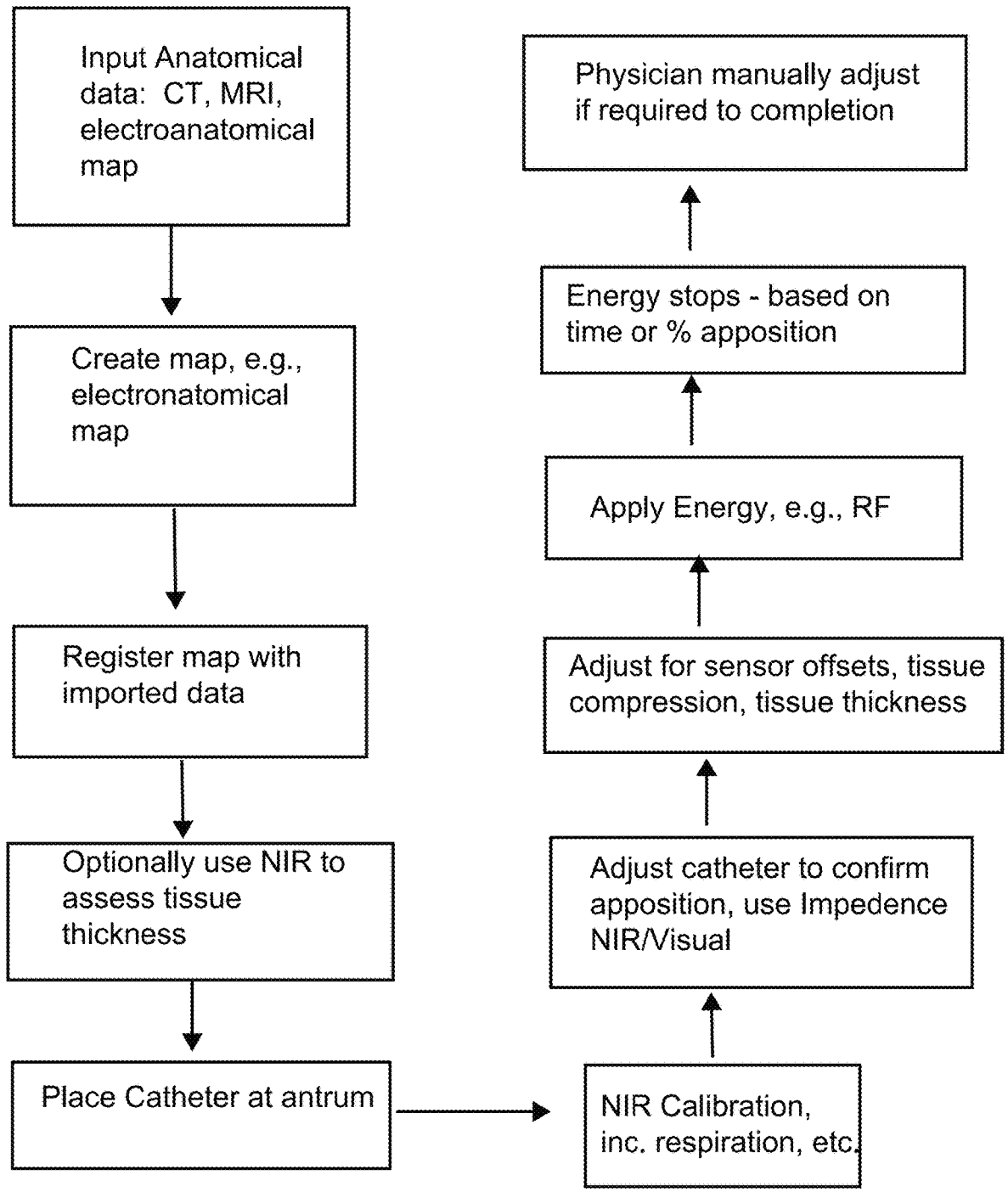
FIG. 23 shows a flow chart according to the present invention.

Hypertension affects 1.2 billion people worldwide. 9% of hypertension patients are drug resistant. One proposed treatment is the ablation of the renal sympathetic nerves. However, there is no end point with current ablation devices for carrying out renal denervation. This can lead to application of too much power for too long a duration, leading to collateral damage. Using OCT, investigators have recorded thrombus formation and even dissection of the renal artery. The renal nerves are located in the adventitial tissue at depths of more than 4 mm. The literature has documented the correlation of nerve firing activity with light scattering indices such as birefringrence and OCT. With birefringrence the current invention is modified to include polarizers, one for the illuminating light and one for the receiving optics. In addition, with reference to FIG. 22, live nerve firing activity is measurable under NIR spectra. Accordingly, nerve stimulation can be utilized with the present invention to determine when the nerve has been fully ablated.

The present invention can provide an endpoint for ablation for locating the depth where the renal sympathetic nerves are located using the NIR signature for nerves to track it. Once the depth of the nerves is located, for example at 4 mm, ablation is carried out. The rate constant for the thermal denaturation of nervous tissue is determined experimentally and used to guide the ablation process as described in the atrial fibrillation process. By way of a non-limiting example, the following represents a preferred algorithm for renal denervation: Femoral artery access→Steerable sheath guided into renal artery with fluoroscopy→Steerable sheath withdrawn→Basket expands to preformed shape→Basket withdrawn until it abuts tightly against the renal artery with the radiopaque markers on the electrode signifying the desired position of the electrode just before the trifurcation of the renal artery→illumination optic fiber is fired→Receiving optic is translated by galvanometer→NIR spectra is compared with NIR spectra of fat stored in memory→Adventitial fat layer identified→Spatial offset at which this occurs is noted→Spatial offset adjusted to a lower offset until a more superficial layer of muscle just adjacent to the adventitial fat layer is identified→Ablation is performed→Rate of change of normalized reflectance is followed as an exponential curve and the lag phase, the slope of the curve of the current reaction is compared against the reaction where 100% transmurality was obtained at a temperature of 60 degrees Celsius over a duration of 40 seconds→If the slope is less than the one stored in memory, computer algorithm then commands the energy delivery unit to increase the power until the slope matches the one for the ideal reaction rate stored in memory.

Ventricular Tachycardia Ablation

For ventricular tachycardia ablation, the tissue to be ablated is thicker. Therefore a bigger spatial offset of 30 to 35 mm between the illuminating and receiving fibers will be required. This can be offset by being able to use a basket with a bigger diameter or a longer catheter in the larger cavity of the ventricle. Likewise, the offset can be increased by using an illuminating fiber on one spline, and a receiving fiber on a second spline. The optical sensor may further be adapted wherein the optical sensor is adapted to perform transmission spectroscopy by utilizing a plurality of basket catheters, wherein one basket catheter is placed in the pericardial space adjacent to a basket in the ventricular cavity wherein the optic fibers of the basket in the pericardial space are adapted to receive light from the illuminating fibers from the basket in the ventricular cavity.

Adaptation for Transmission Spectroscopy

The optical sensor may be adapted to perform transmission spectroscopy by utilizing a plurality of basket catheters, wherein one basket catheter is placed in an adjacent vein, for example the coronary sinus vein to the left pulmonary veins or in the superior vena cava to the right pulmonary veins, wherein the optic fibers of the basket in the coronary sinus or superior vena cava are adapted to receive light from the illuminating fibers from the basket in the left or right pulmonary veins (or vice versa).

The optical sensor may further be adapted wherein the optical sensor is adapted to perform transmission spectroscopy by utilizing a plurality of catheters or basket catheters. For example one catheter is placed in the pericardial space adjacent to a basket in the ventricular cavity wherein the optic fibers of the catheter in the pericardial space are adapted to receive light from the illuminating fibers from the basket in the ventricular cavity.

Catheter

Figure 2:
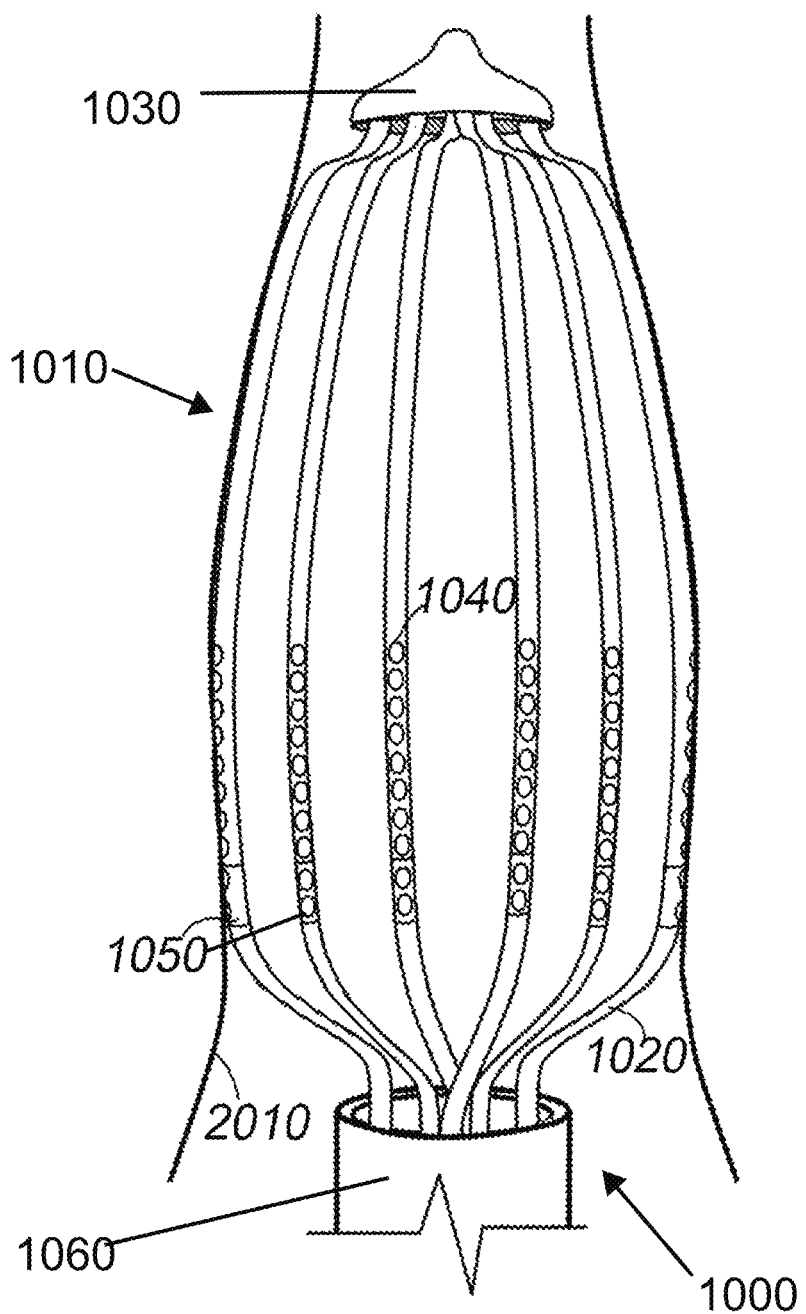
FIG. 2 shows a catheter with a cone shaped basket configuration at the distal end adapted for atrial fibrillation ablation.

FIG. 2 shows one embodiment according to the present invention for determining the properties of a tissue. The distal end 1010 of catheter 1000 expands into a basket configuration with a plurality of arms or splines 1020. By way of non-limiting examples shown in FIG. 4, the basket can have a plurality of shapes, depending on the anatomy it must match, the type of procedure, the ablation locations or the tissue monitoring locations, and the like. In a preferred embodiment, the basket has 8 splines or arms.

FIG. 2 shows the distal end of the catheter with the basket. The distal end of each of arms 1020 is attached to a soft, non-traumatic cap 1030 and is preferably made of Pebax which has been doped with a radiopaque material like Barium Sulfate.

The basket configuration can include wires, ribbons, cables and struts and can be constructed from metals, non-metals or combinations of both. The basket configuration can be coated with the Duraflo. Elements of the basket configuration can be made of one or more materials, including both metals and non-metals. Typical metals chosen for basket construction include but are not limited to nitinol, stainless steel, elgiloy, other alloys or any combinations thereof. The distal basket of the catheter has a preformed flexible shape which is designed to conform to the vessel 2010 in which the basket is placed. For atrial fibrillation ablation, the basket may be shaped like a cone to "abut" the pulmonary vein.

Catheter 1000 includes a plurality of tubular components that can be steered by including a controllable pull wire at or near the distal end (not shown). Specifically, the catheter of the present invention can include an integral steering means such as a plurality of pull wires attached near a distal portion of the catheter and operably attached to a lever, knob or other control integral to a handle of the catheter. The steering mechanism is used to deflect the basket (used in conjunction with an outer sheath 1060 which may or may not be steerable) and distal end of the catheter into the left and right pulmonary veins of the left atrium. The integral catheter steering means can be used with a steerable transseptal sheath, e.g., outer sheath 1060. A plurality of pull wires can be mounted, e.g., 90 degrees apart at different locations in a distal portion of the catheter to provide multi-axis, precision controlled steering.

Figure 3:
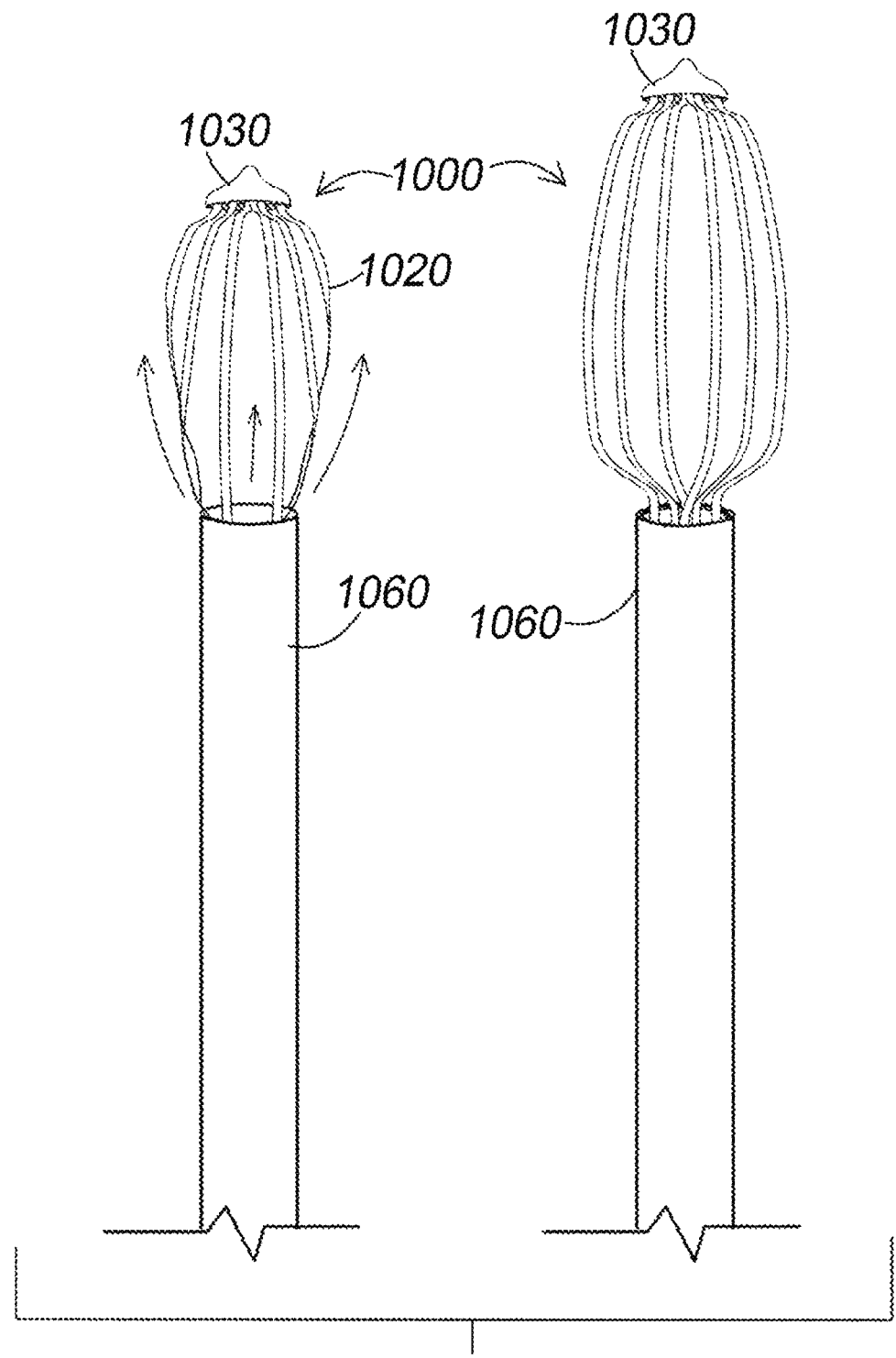
FIG. 3 shows a basket catheter delivered to the target site in a partially "collapsed" configuration within a sheath and exiting the sheath.
Figure 5:
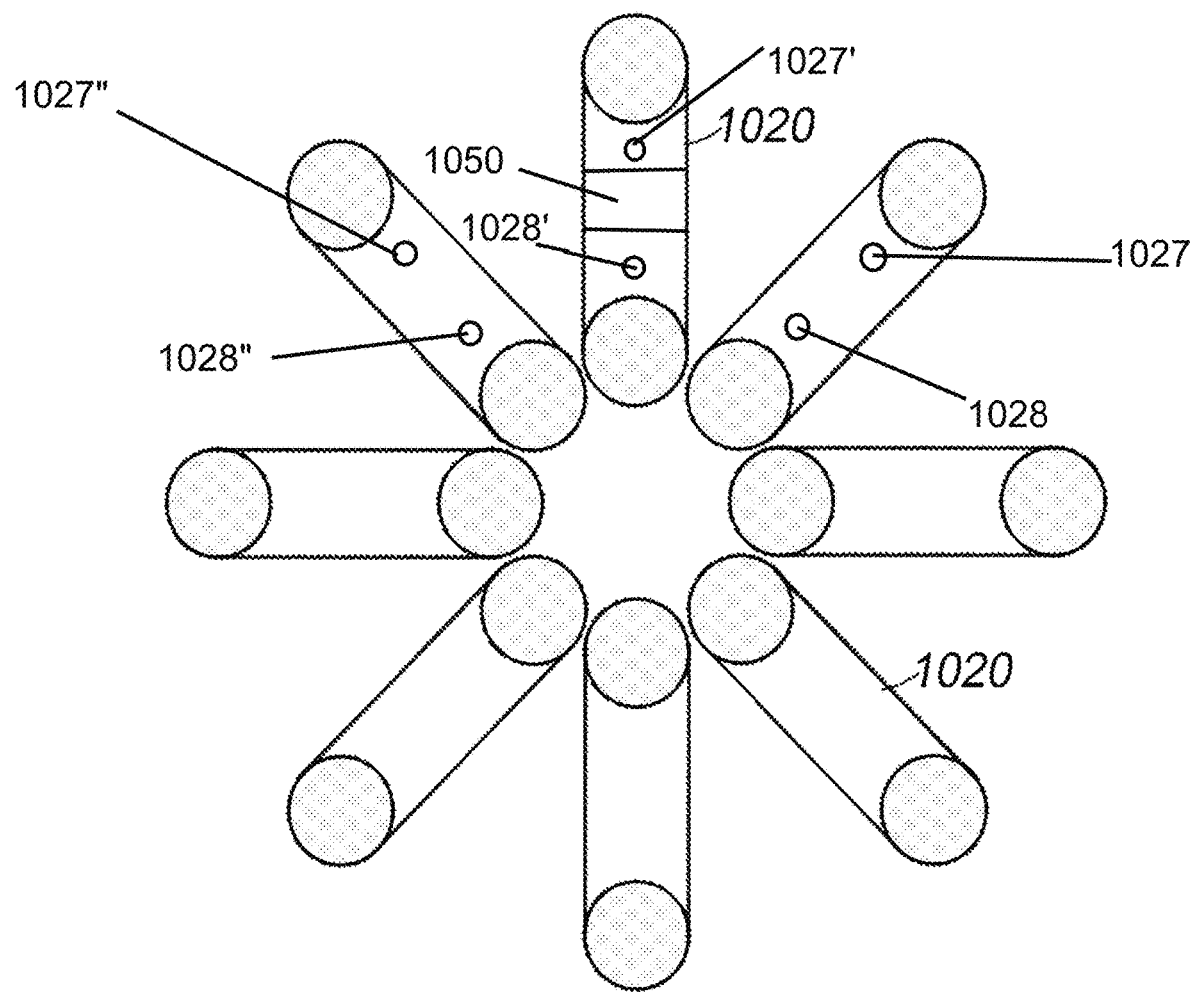
FIG. 5 is an end-on view of a basket catheter according to an embodiment of the present invention.

Basket 1010 is introduced into the pulmonary vein via the deflectable sheath 1060 (for example the Agilus™ sheath, St Jude). As shown in FIG. 3, the sheath is then withdrawn and the basket is allowed to expand fully to its preformed shape. FIG. 5 shows the end-on view of the basket. As seen in FIG. 2, the basket will closely hug the contours of the vein. The basket is adapted to be deformable such that when the outer steerable sheath is withdrawn, the basket will expand to its maximum diameter to "abut" and press tightly against the conical portion of the anatomy it is in, e.g., the pulmonary vein which extends from the os of the vein to approximately 20 mm into the vein.

The basket is adapted with this linear segment of the basket designed with a series of optional drilled apertures 1040. In one embodiment the apertures measure 300 micrometers each and separated by 760 micrometers. The apertures may enclose optic fibers 1027, 1028 (FIG. 11) for performing spatial offset diffuse reflectance spectroscopy.

Ensuring close contact between basket and tissue, maintaining stability, and maintaining a substantially constant contact pressure is important for optical sensing as motion artifacts and different contact pressure can affect optical sensing data. In one embodiment the invention is preferably shaped in such a fashion as to bias the splines 1020 into a relatively constant degree of contact with the tissue. The splines 1020, the cap 1030, the sheath 1060, and the catheter 1000 may all cooperate to orient the splines toward the tissue, place the splines in contact with the tissue, and retain the splines in position during movement. In many situations, e.g., when working within a beating heart, the tissue itself is moving. In these situations the catheter's goal is to reduce the relative motion between the spline and the tissue. In particular, to reduce the relative motion between the apertures 1040 or the optical fibers 1027, 1028 and the tissue.

In another embodiment the invention comprises a retention means to ensure that the contact remains constant. Retention means can employ suction, biasing agents, hooks, screws, or the like to enter the tissue and hold the spline 1020 in place, steering from the catheter or sheath, or other means to retain the spline and the fiber optics in a relative constant contact and spacing to the tissue.

In another embodiment, the invention compensates for increased or reduced contact pressure by, for example, employing contact sensing means to determine when the contact is sufficient to take a reading, or by adjusting the reading based on the degree of contact. A number of contact sensing mechanism are contemplated, including piezoelectric contact sensing, fiber optic based contact sensing, proximity sensors, electrodes, electro anatomical mapping systems, MEMS based contact sensing, and other force or movement based contact sensing.

In one embodiment the system of the invention is designed to alert the operator if the degree of contact has changed, has become insufficient, or has become excessive. Such alerts can be an audible alert, tactic feedback, computer visual output, e.g., on an electroanatomical map. In another embodiment the system automatically recalculates the algorithms based on the revised degree of contact and/or the previously recorded degree of ablation.

Figure 7:
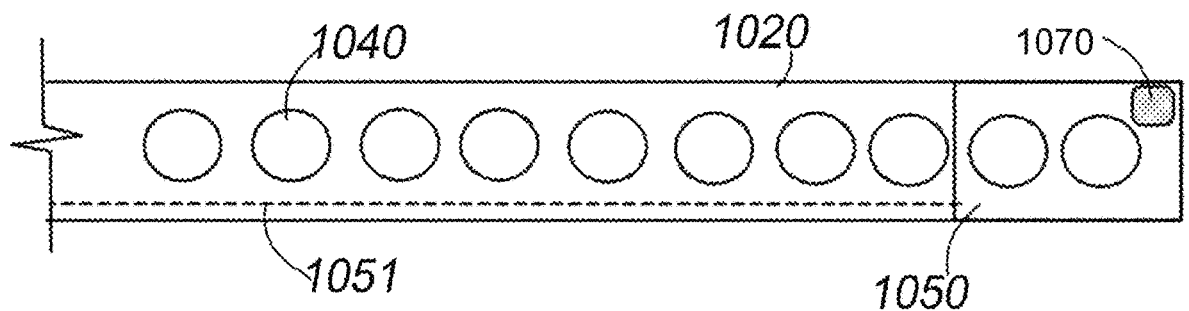
FIG. 7 depicts the structure of a nitinol spline tubing in an alternative basket configuration.
Figure 8:
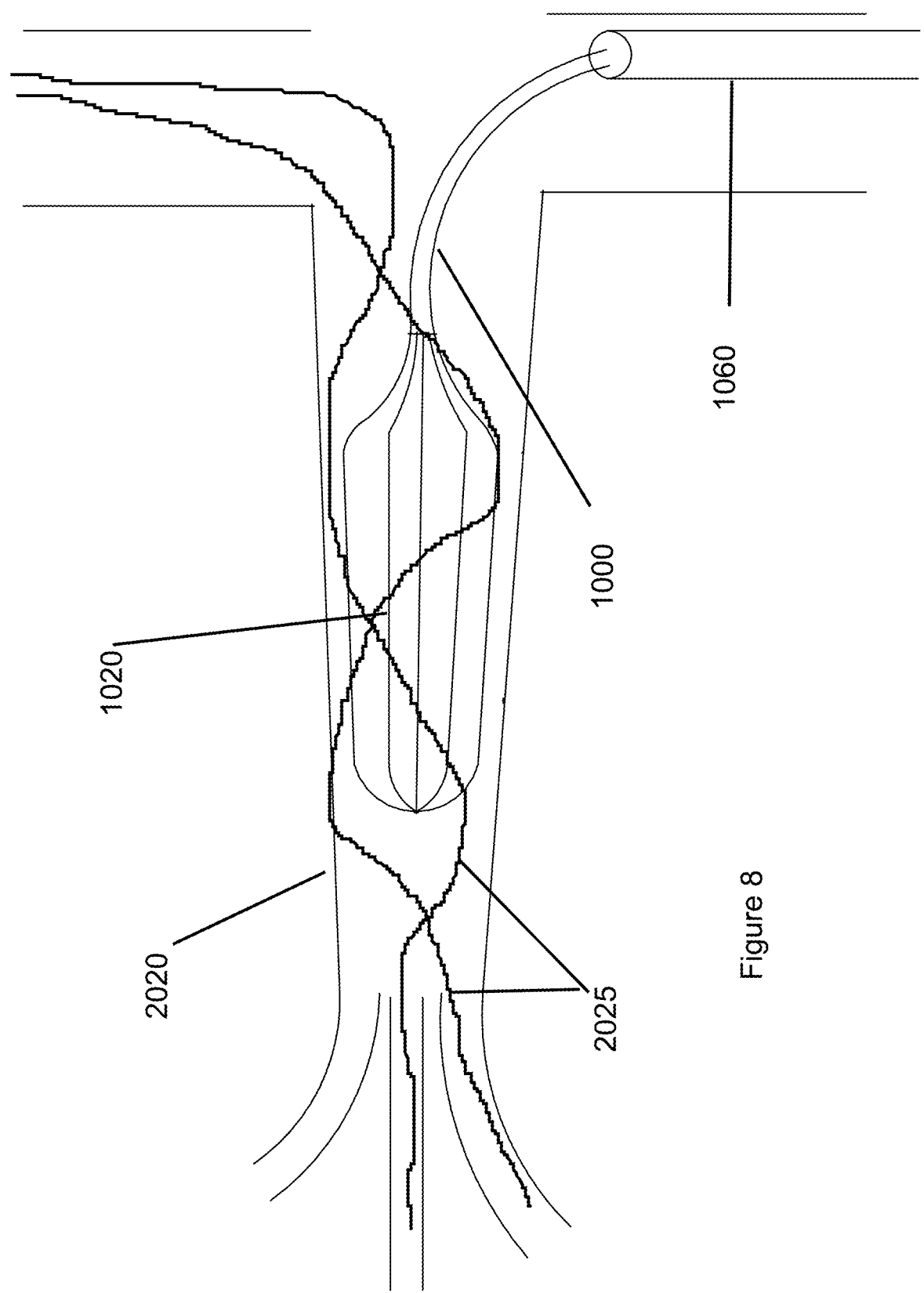
FIG. 8 shows a basket catheter used for renal denervation where the shape of the basket is rectangular or cylindrical, to conform to the tubular structure of the renal artery.

In an embodiment of a basket catheter 1000 that can be used for renal denervation, the shape of the basket is rectangular (when viewed in 2D, or cylindrical, in 3D), to conform to the tubular structure of the renal artery 2020 (FIG. 8) with nerves 2025. For renal denervation, the size of the basket typically ranges from 2 mm to 6 mm in diameter and has a longer flat, linear segment (FIG. 8). The size of the basket can range from 2 mm to 70 mm in diameter. The splines 1020 may range from 45 mm to 70 mm from the distal end of the basket and may attach to the soft atraumatic cap 1030 at their distal end. In a preferred embodiment, holes 1040 (FIGS. 6, 7) are drilled into each arm or spline with the spacing of each of the holes being predetermined, or known. For example, holes 1040 may be 760 micrometers from each other. In this embodiment, each of the splines of the basket may contain a number of apertures 1040 (10 shown for illustrative purposes) for allowing light from the illuminating optic fiber(s) to illuminate tissue and the receiving optic fiber(s) to receive light from the tissue. The diameter of the holes depends on the needs of the fiber and the application, but in one embodiment is 300 micrometers. The holes can have a 300 micrometer ball lens (e.g., as manufactured by DSI) to collimate and focus the returning light from the tissue to the receiving optic fiber wherein the ball lens is bonded to the hole by epoxy.

Figure 6:
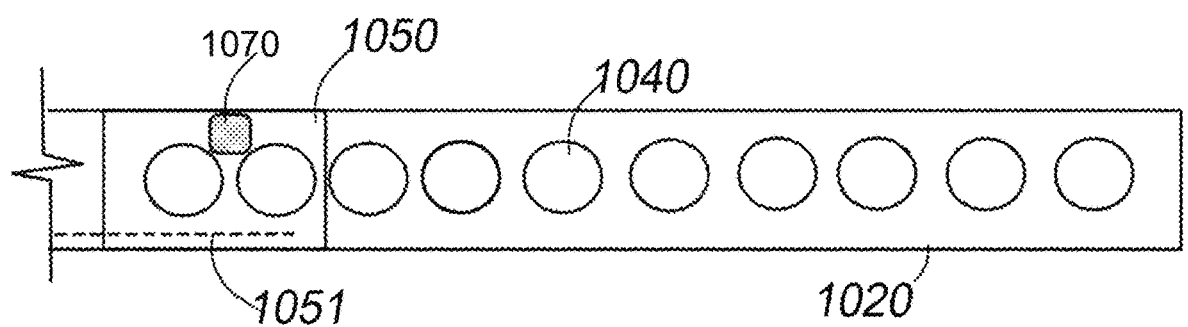
FIG. 6 depicts the structure of a nitinol spline tubing in a basket catheter configuration.

An energy application element may optionally be integrated into the catheter 1000 wherein energy application element consists of electrodes 1050 for applying energy to the tissue. The electrodes are connected to an energy source, e.g., an RF energy source, via electrical connections for providing electrical energy to the tissue. The electrical connections are preferably wires located within the catheter. For example, as shown in FIGS. 6 and 7, the two distal most holes have electrodes 1050. Any type of electrode may be used, including ring electrodes, spot electrodes, printed electrodes, or patterned electrodes. Any biocompatible electrode material may be used, including platinum, gold, silver, and alloys thereof.

While in this embodiment the electrodes 1050 are pictured as being the distal most elements, in a preferred embodiment each electrode has a fiber optic that terminates to its proximal side and a fiber optic that terminates to its distal side (or one that can be moved along a path that includes spline portions to each respective side). Accordingly, the electrodes 1050 may in fact be in the middle of the apertures and the fibers. The specific electrode locations will depend on the needs of the procedure, the depth of the tissue to be interrogated, and the location of the tissue to be ablated. Thus, for example, there may be two fiber optics and apertures terminating proximally of the first electrode, a third fiber optic between the two electrodes 1050, and additional fibers terminating distally of the electrodes.

Figure 9:
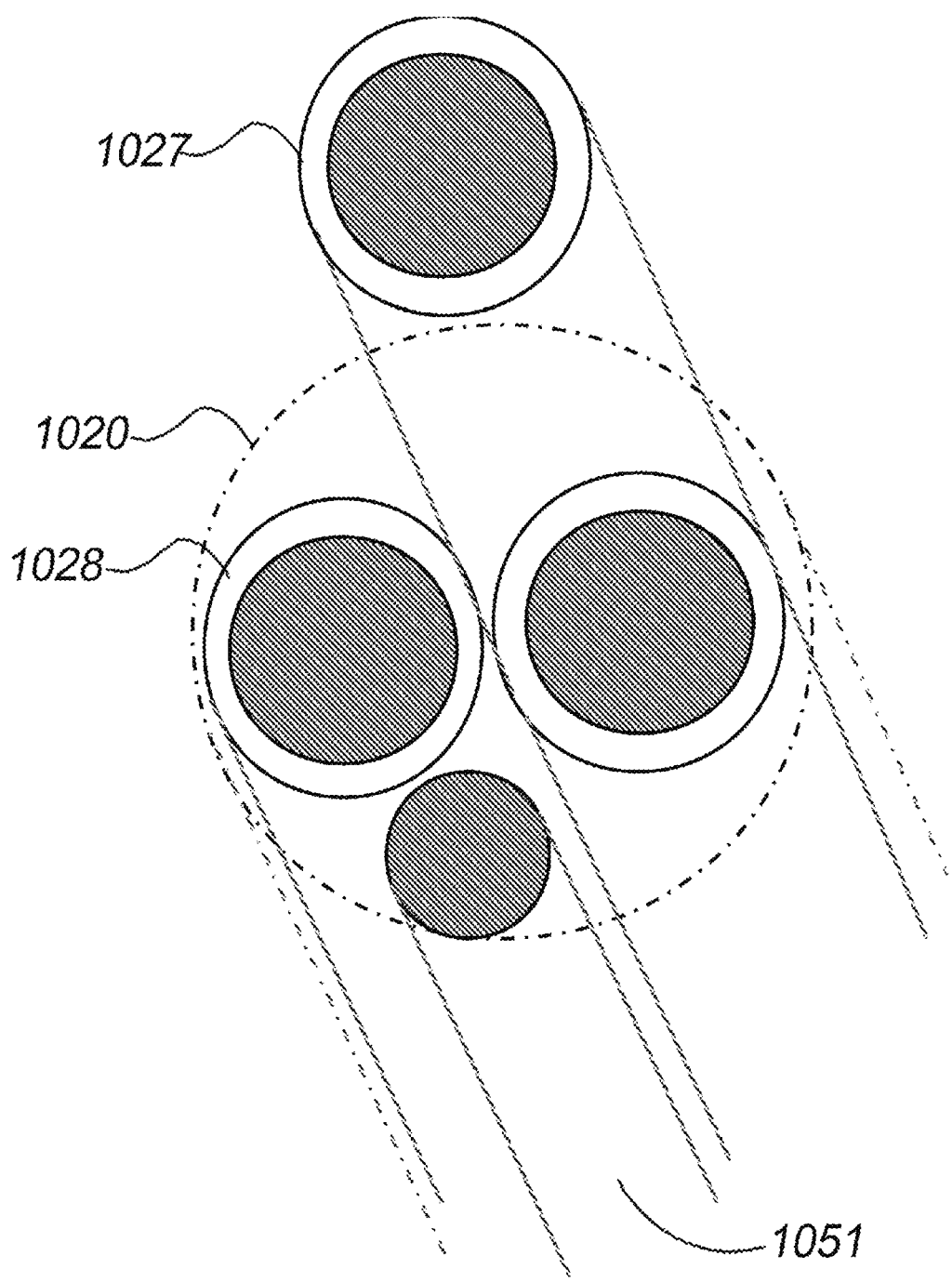
FIG. 9 shows a cross section of a spline for a catheter.

In one embodiment, electrodes of a platinum-iridium alloy are mounted to the arms with cyanoacrylate or other adhesive beads. Each electrode carries a thermocouple, preferably a copper-constantan wire junction welded to the internal surface of the electrode. Each electrode, and any included thermocouple is attached to one or more wires to form a wire bundle, which travels proximally and is attached to an electrical port on the proximal end of the ablation catheter. A copper wire 1051 (50 to 100 micrometers in diameter) runs on the inside wall of the spline to connect to the electrode. (FIG. 6, FIG. 9). Each of the electrodes is attached via connecting wires and one or more connectors such as a conduit to an energy delivery apparatus, preferably an RF energy delivery unit, which is also attached to a patch electrode but preferably a conductive pad attached to the back of the patient. The energy delivery unit may be configured to deliver RF energy in monopolar, bipolar or combination monopolar-bipolar energy delivery modes, simultaneously or sequentially with or without "off" or no energy delivered time duration.

In a preferred embodiment, the energy delivery unit is configured to provide electrical mapping of the tissue that is contacted by one or more electrodes integral to the basket. Alternatively, a separate mapping unit such as a MEMS gyroscope 1070 or another sensor 1070 may be used, preferably attached to the catheter simultaneously with attachment to the energy delivery unit (FIGS. 6 and 7), in which case, a copper wire 1051 also runs to the MEMS gyroscope 1070 or sensor 1070.

While the energy delivery unit has been discussed as an RF energy delivery unit, the energy delivery unit may use ultrasound energy (and accordingly ablation electrodes 1050 would be replaced by piezoelectric elements), cryogenic freezing mechanisms, laser energy, microwave energy, or chemical ablation. The targeted tissue may be destroyed, ablated, or otherwise treated by different mechanisms depending on the energy delivered. For example, and RF electrode may primarily operate to heat the tissue to kill the cells. Likewise, a laser may primarily heat the tissue, and as with the RF electrode thermally denature the cells. Cryogenic freezing, on the other hand, may likewise denature the tissue by the formation of intracellular ice crystals. Ultrasound energy, on the other hand, may primarily operate to mechanically deconstruct the cells. Each mechanism may be measured and monitored by reflectance, but the specific spectrum used and calculations may need to be adjusted, both for the mechanism used, as well as for the power, size of energy delivery, and its concentration. For example, a focused laser may provide thermal denaturation just as the RF electrode would, but due to its narrow focus may provide a more narrow ablation pathway, and a more rapid ablation pathway.

The catheter of the present invention has an optical sensor integrated into it possessing a light emitting means and light receiving means. The optical sensor is adapted to generate optical sensing data depending on the received light. In one embodiment the light emitting and receiving means of the optical sensor comprise optic fibers. Illuminating optic fibers 1028 are connected to a light source such as a laser, an LED (for example an LED made by Allied Electronics, part no SML-P12YTT86), or another source and the optic fibers guide the light to the tissue. The collection fibers 1027 are preferably connected to a spectrophotometer for generating optic spectra of the tissue wherein the invention is adapted to determine the characteristics of the tissue for example transmurality, of the ablation lesion depending on the characteristics of the optic spectra. A plurality of optic fibers may be enclosed within each of the arms or splines 1020. One manufacturer of suitable optic fibers is (Polymicro, Arizona). In a preferred embodiment the diameter of the optic fiber may be 200 micrometers but can range from 100 to 600 microns. The fibers can be a multimode fiber. The fibers can have a numerical aperture of 0.22. Within a hollow tube of each of the arms or splines, the optic fibers are placed next to each other (FIG. 9), one on top of each other, or as needed for the specific device and procedure. The optic fibers can be covered or coated with PVC or polyamide to prevent crosstalk between the fibers.

In cases of atrial fibrillation ablation for example, the illuminating optic fiber is preferably proximal to the receiving fiber. The illuminating optic fiber can be movable/translatable or fixed through application of cement (e.g., Norland 93, Norland Products) to the inner wall of the hollow tube of the arm or spline (FIG. 10). The receiving optic fiber can likewise be fixed or movable, and can be adapted to achieve a linear and rotational scan of the tissue by translating the optic fiber through a range of a linear distance between 2 to 20 mm and a rotation of between 10 to 60 degrees respectively.

Figure 11:
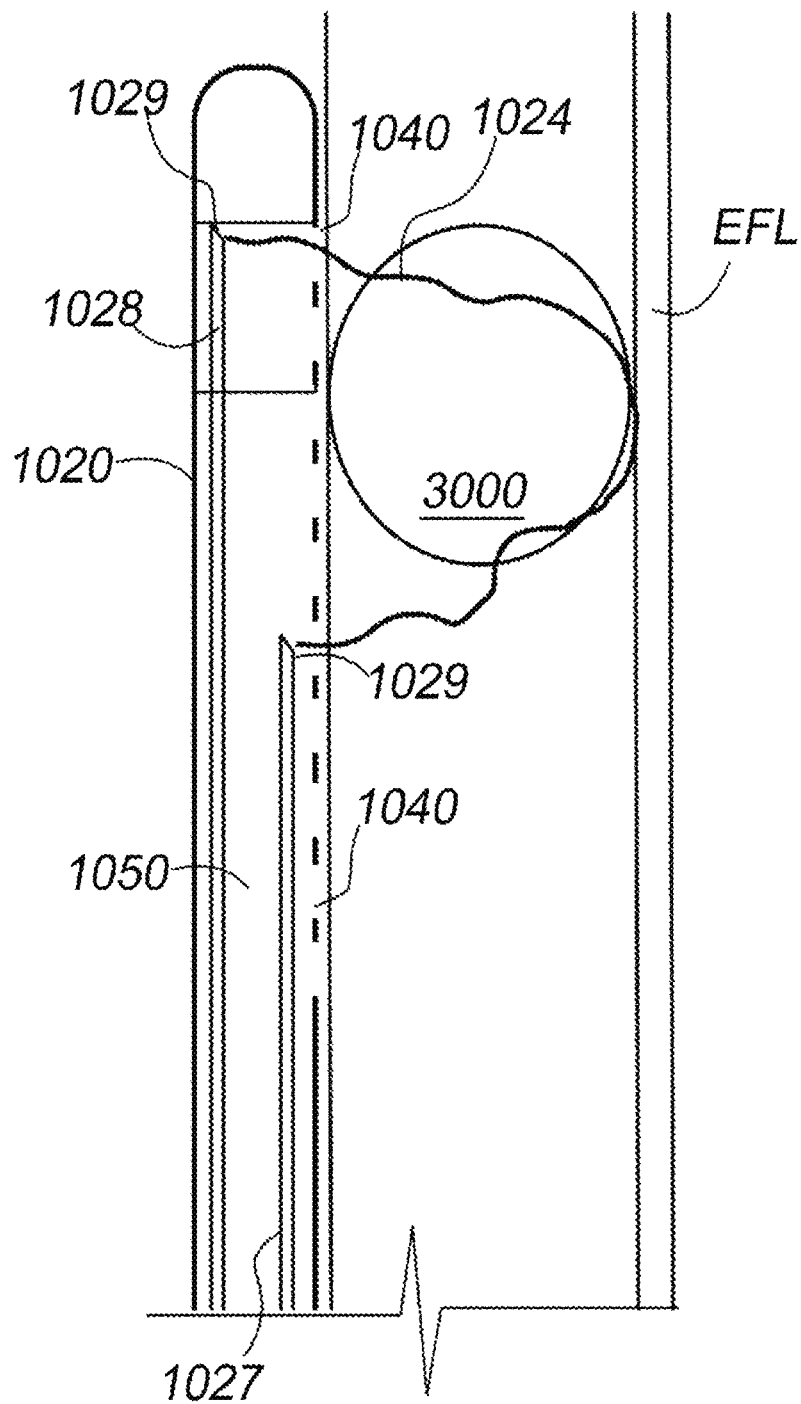
FIG. 11 shows a cross section of a hollow tube of a catheter or spline, and optic fibers therein.

For renal denervation, the illuminating optic fiber 1028 is preferably distal to the receiving fiber (FIG. 11). The receiving optic fiber is preferably not fixed but movable, and can be adapted to achieve a linear and rotational scan of the tissue by translating the optic fiber through a range of a linear distance between 2 to 20 mm and a rotation of between 10 to 60 degrees respectively. The driving force for the scan is provided by a linear/rotational galvanometer (e.g., from GSI Lumonics, Wilmington, Mass.).

The translation provided by the linear galvanometer is transmitted to the tip by a polytetrafluoroethylene coated polyimide tube (Microlumen, Tampa, Fla.) containing the receiving optical fibers (FIG. 9).

The fiber optics can be oriented to illuminate the tissue and receive reflectance from the tissue in a number of manners. In one embodiment they are directly pointed at the tissue. In another embodiment, the galvanometer can also rotate the receiving and illuminating optic fibers to scan unablated areas on either side of the ablated area to provide an assessment of the area ablated. Both the illuminating and receiving optical fibers are adapted to illuminate the inner wall of the heart in a sideward looking direction. In another embodiment, light is coupled out from an optical fiber in a certain angle; e.g., 43 degrees, by polishing a slanted distal end on the respective optical fiber and by coating the surface at the slanted end with a metallic layer. Both the receiving and illuminating optic fibers comprise a core and a cladding. On the polished slanted end surface of the optical fiber, a metallic coating is provided for forming a mirror 1029. The metallic coating can be, for example, a layer of approximately 100 nm of silver on a chromium adhesion promoter layer of approximately 5 nm. The light from the illuminating optic fiber is guided along the light path such that it is reflected by the mirror in a sideward looking direction. Light travelling back from the tissue at the receiving optic fiber similarly passes through the apertures into the distal end of the fiber and is reflected by the mirror back along the axis of the optic fiber. The returning light from the tissue may be collimated by a ball lens into the slanted end of the receiving optic fiber. The apertures can also be adapted for providing irrigation, or configured to provide varying degrees of stiffness along the spline such as deployed in slotted hypotubes.

The present invention comprises an irrigation control unit being connected with the irrigation openings via an irrigation tube in order to allow the user to control irrigation of the cardiac tissue.

4D Electroanatomical Mapping System

Embodiments of the current invention comprise a localization unit for localizing the ablation electrode, the catheters, the fiber optics, and other relevant components. In one embodiment the localization unit (LU) comprises a MEMS gyroscope which is attached to the basket catheter, a system like the Microsoft Kinect™ System and a fluoroscopy system. An Inertia Monitoring Unit (IMU) for inclusion in the proposed system includes motion sensors and a MEMS gyroscope incorporated at each of the electrodes on each of the arms or splines of the catheter which permits point by point localization of the catheter tip position and also improved stability of the catheter system. The motion sensors may be any device capable of generating a signal that is indicative of the orientation or the rate of change of orientation of the sensor. The generated signal is preferably nearly proportional to the orientation or rate of change of the orientation of the sensor, but other dependencies are within the scope of the present invention. For example, a sensor may be a liquid level pendulous tilt sensor, a physical gyroscope, a solid-state gyroscope, an accelerometer, or a pair of proximity sensors arranged in a line and separated by a known distance. Lightweight accelerometers and lightweight body sway sensors, such as velocity transducers or sensors may also be used or included as part of the sensors. In addition, microelectro-mechanical systems (MEMS) accelerometers, piezo-electric accelerometers, or other rotation and/or linear accelerometers can be used. In various embodiments of the present invention, a solid-state gyroscope is used with a liquid level tilt sensor. The liquid level tilt sensor may be used to correct for drift in the solid-state gyroscope.

A preferred embodiment of the invention includes a MEMS gyroscope because of its small size and low cost. A plurality of motion sensors and/or gyroscope(s) can monitor the position of the ablation catheter, fiber optics, and electrodes, and feed signals to a processor. Preferably, the processor can perform a 3×3 matrix multiplication to computationally determine the roll, pitch and yaw. In a preferred embodiment, the motion processor then transmits the results from this computation to a holographic projection system, such as the Microsoft Kinect™ system. The data from the computation will include x y and z coordinates which will be plotted into a holographic projection. In a preferred embodiment, at each point where x y and z coordinates are being generated, Near Infrared, NIR, Raman, Fluorescence spectroscopy, birefringence, and OCT can be performed to collect depth data, which is the depth of the muscle tissue at a particular point. The processor will input the data from the Raman spectroscopy and calculate the depth data and use the depth data to translate the x y and z coordinates into an outer shell of the cardiac silhouette, creating a 4D image of the heart. At the beginning of the ablation procedure, fluoroscopy images will be taken in the right anterior oblique and the left anterior oblique views. The LAO and RAO views will be used to reconstruct a 3D image. A computer algorithm will then transform the 3D data into Cartesian coordinates (x, y and z data). The basket catheter is then placed in the pulmonary vein/renal artery and a fluoroscopy image is taken. This will serve as the initialization point for the MEMS gyroscope. The location of the eight electrodes is therefore registered by the gyroscope. The gyroscope requires no external reference once it is initialized. As ablation is carried out, depth information from spatially offset diffuse reflectance spectroscopy is integrated with the 3D data to generate a 4D image.

For example, at the beginning of the procedure, excitation of the tissue by the illumination optic fiber is performed and scanning is performed by the receiving optic fiber by translating the receiving optic fiber with a motorized linear galvanometer. The optical spectra obtained in real time is compared against stored optical spectra for fat. The correlation between actual depth of the epicardial fat layer and the spatial offset is determined histologically in ex vivo and in vivo experiments. The depth of the tissue at which the epicardial fat layer is detected relates to the spatial offset between the illuminating and the receiving optic fibers and this information is relayed to the gyroscope which registers this as depth information on the 3D Cartesian coordinate system. The spatial offset is then adjusted to detect the muscle layer that is just superficial to the epicardial fat layer again by comparing the optical spectra from the live on line data with stored optical spectra for muscle. The spatial offset at this depth is registered by the gyroscope. Ablation is then carried out.

Embodiments of the present invention are adapted to monitor the rate of change of reflectance as thermal denaturation is occurring. The rate of change of reflectance corresponds to the proportion of tissue that is being denatured. For a given temperature and a given rate constant, we can determine the time duration needed for 100% tissue denaturation to occur. Therefore, at each time point, the invention is adapted to indicate the proportion of tissue that has been denatured. This information can be calculated to give the depth. This depth info is sent to the gyroscope which then displays on the user interface the progression of the zone of damage as an M mode image.

In an ablation catheter with 8 splines, each having an electrode and a diagnostic insert with optical illuminating and receiving elements, once the first set of ablation is done, the location of the first set of 8 ablation points is registered by the gyroscope and the basket is rotated clockwise or counterclockwise to continue the ablation. Using a configuration of 8 arms/splines, 2 or 3 rotations may be required to achieve a circumferential ablation around each pulmonary vein. Alternatively, in another embodiment, the invention may be adapted to provide a basket with between 16 to 20 splines to achieve circumferential ablation with "1 shot" ablation.

Ablation Catheter

As shown in FIG. 10, the end of the illuminating fiber 1028 (see mirror 1029), the ablation electrode 1050, and the end of the receiving fiber 1027 are all successively laid alongside tissue 3000. While many types of catheters can be used for cardiac ablation, one of the most common ablation catheter types is a linear catheter with one or more ablation electrodes on the distal end. This basic form can be modified to function according to the present invention. FIG. 10 shows a such a standard linear catheter, modified for the inventive procedure.

Numerous other devices will be illustrated herein, with the common goals of providing illuminating fibers and receiving fibers that are (1) sufficiently spatially offset along the length of the tissue (2) laid alongside the tissue, e.g., in contact or near contact with the tissue, and (3) in a stable relationship to the tissue, especially a stable spatial relationship.

Spatially Offset

As shown in FIG. 10, the catheter 1000 comprises a catheter body 1020 which is generally linear. The catheter body may also be pre curved, or may be curved by the use of a stylet or pull wires. Catheter body 1020 includes an electrode 1050, which may be a ring electrode, spot electrode, printed electrode, or other type of electrode. Likewise, another ablation source may replace electrode 1050, such as piezoelectric elements for ultrasound ablation, a laser mechanism, cryo ablation mechanism, microwave elements, or a port for chemical ablation. While catheter 1000 is drawn in its most basic form, it should be understood that the catheter 1000 may preferably include a handle at its proximal end for controlling the location, movement and orientation of the catheter 1000, pull wires, stiffening agents, braiding, irrigation ports and lumens, radiopaque materials and location sensors.

In particular, catheter 1000 may comprise sensors 1035 which function with a guidance system to identify where the catheter is, and preferably, where the fibers 1027, 1028 terminate. For example, sensors 1035 may comprise magnetic coils, electrodes, ultrasound markers, radiopaque markers, or other sensors that are on the catheter body. The sensors 1035 work with a guidance system to determine the actual distance between the terminal ends of each fiber, and thus can determine if the catheter is straight (and thus the offset is at its original length) or is bent, and thus at a reduced spatial offset. In a preferred embodiment the sensors are on the catheter body 1020. In another preferred embodiment the sensors are attached (directly or functionally) to fibers, 1027, 1028 to mirrors 1029, or to the terminal ends of fibers 1027, 1028.

While it is preferred that the catheter include an ablation element 1050, in another embodiment catheter 1000 is part of a system, and the ablation means is absent entirely, or present on a second catheter, or on a different spline or portion of catheter 1000.

Catheter 1000 may further include one or more apertures 1040. In one embodiment the apertures 1040 are drilled. They may measure 300 micrometers each and be separated by 760 micrometers. The apertures may enclose optic fibers 1027, 1028 for performing spatial offset diffuse reflectance spectroscopy. The apertures may be covered by a plastic or glass lens or transparent heat shrinks. In another embodiment apertures 1040 are not present, and instead the wall of catheter body 1020 is optically transparent to the optical radiation emitted by the fibers or other source.

Catheter 1000 further includes illuminating fiber 1028, which includes mirror 1029 on its distal end. Mirror 1029 orients the emissions from fiber 1028 toward the tissue. Catheter 1000 further includes receiving fiber 1028, which includes mirror 1029 on its distal end. Mirror 1029 orients the reflectance and other emissions from the tissue toward fiber 1028. In some embodiments the mirror 1029 is absent, and instead a slant or angle is cleaved into the distal tip of the optic fiber. Of course, different angles can be cleaved into the fibers to achieve different angles of incidence of light on tissue and also different angles of reception of light from the tissue.

While catheter 1000 is depicted with mirrors 1029, in the alternative the fibers may be turned toward the target tissue and the mirror may be absent. Other means may additionally focus or orient the optical signals toward the tissue or fiber as needed. For example, one optical fiber can be used for both the illuminating and receiving fiber, but with a beam splitter or a two way mirror placed at the location where the illuminating radiation exits and a receiving mirror 1029 placed where the radiation returns to the fiber. Because the intensity of the light may be attenuated using a beam splitter, this embodiment may be advantageously deployed with larger diameter optic fibers.

The emission from illuminating fiber 1028 passes through the ablated tissue in a "banana" shape, and back out to the receiving fiber 1027. Applicant has found that the longitudinal distance between these fibers 1027, 1028 is the key to measuring the transmurality of the lesion, as, for example, a 10 mm longitudinal distance is needed to measure a 5 mm thick tissue. The specific offset required will depend on the tissue being measured. In particular, for the heart the atria are thin walled chambers, while the two ventricles are very thick walled chambers. While the atria typically have a maximum muscle thickness of 5 mm, and thus an offset of 10 mm is sufficient, with the ventricles the tissue to be ablated is thicker. Therefore a bigger spatial offset of 30 to 35 mm between the illuminating and receiving fibers will be required.

The tissue thickness in any given chamber will vary. Accordingly, it is advantageous for the device to be able to interrogate tissue at a range of depths. In addition, in one embodiment of the present invention the catheter interrogates the tissue to determine the tissue's thickness. In a catheter according to the present invention it is advantageous if the catheter can measure tissue at a range of spatial offsets. For example, applicants have found that a catheter with an adjustable spatial offset from 2 mm to 30 mm is advantageous. A catheter with a spatial offset that ranges from 2 mm to 30 mm, or in many cases from 4 mm to 16 mm is likewise able to interrogate the tissue in the atrium to determine its depth, as well as to measure the transmurality of the lesion. While a fixed offset catheter (e.g., one with only one offset distance) may only have a 10 mm offset or an 8 mm offset, this embodiment includes a catheter that can adjust to multiple offsets.

Another embodiment of this catheter, the catheter includes multiple fibers at different distances. For example, while FIG. 10 shows the terminal ends of fibers 1027, 1028 being separated by 12 mm, in one embodiment the catheter further includes multiple fibers 1026 (not shown). Each of these fibers has a terminal end spaced 1 mm from the terminal end of the next fiber. Thus, fiber 1028 and the first fiber 1026 are offset by 1 mm, and a transmission from illuminating fiber 1028 that is received back at the first fiber 1026 has penetrated only 0.5 mm into the tissue. The transmission from illuminating fiber 1028 that is received at the second fiber 1026 has penetrated 1 mm, and so on until the fiber 1027 is reached and the tissue has been interrogated between 0.5 mm to 6 mm in depth in 0.5 mm increments. Thus, in this embodiment the catheter may simultaneously monitor the ablation lesion throughout the entirety of the tissue by performing calculations (as per above) for each depth measured.

In other embodiments each fiber is spaced 2 mm from the next, or 0.5 mm from the next. While the above discussion utilizes a fixed illuminating fiber 1027, in another embodiment each of the fibers 1027, 1028, and 1026 can either illuminate, receive, or both (e.g., with signal gating). In such a fashion a wider linear length of the tissue may be measured (providing additional information about the lesion's progress), or a more specific portion of the tissue may be targeted for interrogation. For example, one fiber 1026 can illuminate while another fiber 1026 receives, thereby shifting the location of the tissue interrogation. In one embodiment the physician or operator may indicate which portion of the tissue to interrogate, e.g., via input onto an electroanatomical map. In another embodiment, the system automatically identifies a portion of the tissue to interrogate based on, for example, previous lesion locations, electrical signals from the tissue, or temperature measurements.

In another embodiment, the terminal end of the fiber 1027 may be laterally moved back and forth to increase or decrease the offset from the terminal end of fiber 1028. Likewise, fiber 1028 may the one that is moved. Preferably the moving fiber (or fibers, if both move) is securely and reliably held in place by, for example, a lumen in the catheter body 1020, a sleeve (not shown), or by periodic retaining clips or guides. Regardless of the mechanism, it must either include apertures for optical transmission, or be optically transparent at the relevant wavelengths.

Figure 16:
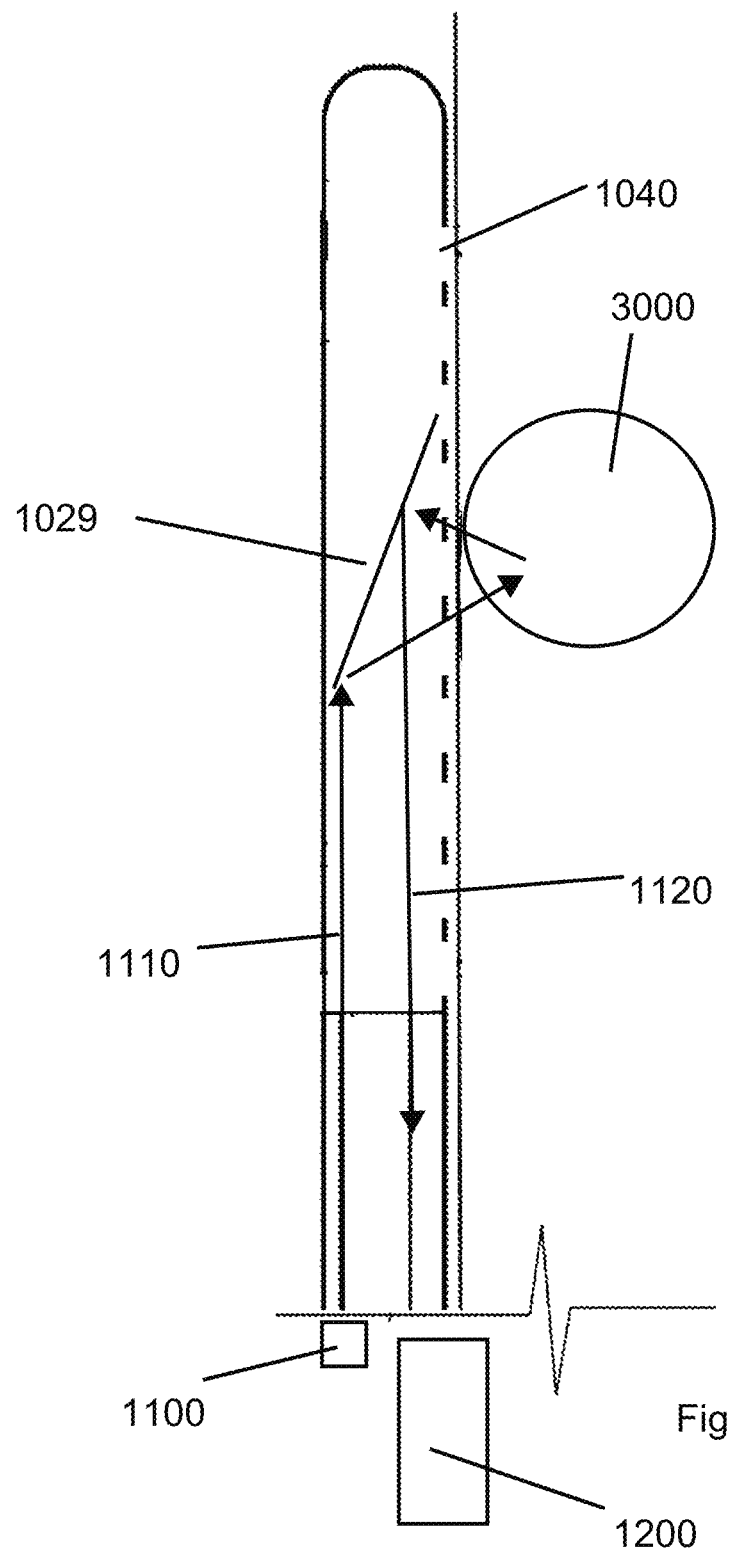
FIG. 16 shows a cross section of a hollow tube of a catheter or spline, and optic fibers therein.

As an alternative to moving the fiber, a mirror 1029 or prism mirror (not shown) may be moved or angled. In another embodiment, shown in FIG. 16, the optical source may be an excitation laser 1100. The laser may reflect its pulse 1110 off a 45 degree angled mirror 1029 (or other angle, depending on the application) and into tissue 3000. The reflectance 1120 is then bounced off the same or another mirror and returned to a spectrophotometer 1200, e.g., a Raman spectrophotometer. The laser source may deliver its pulse to the tissue 3000 via a fiber, e.g., fiber 1210.

Figure 15:
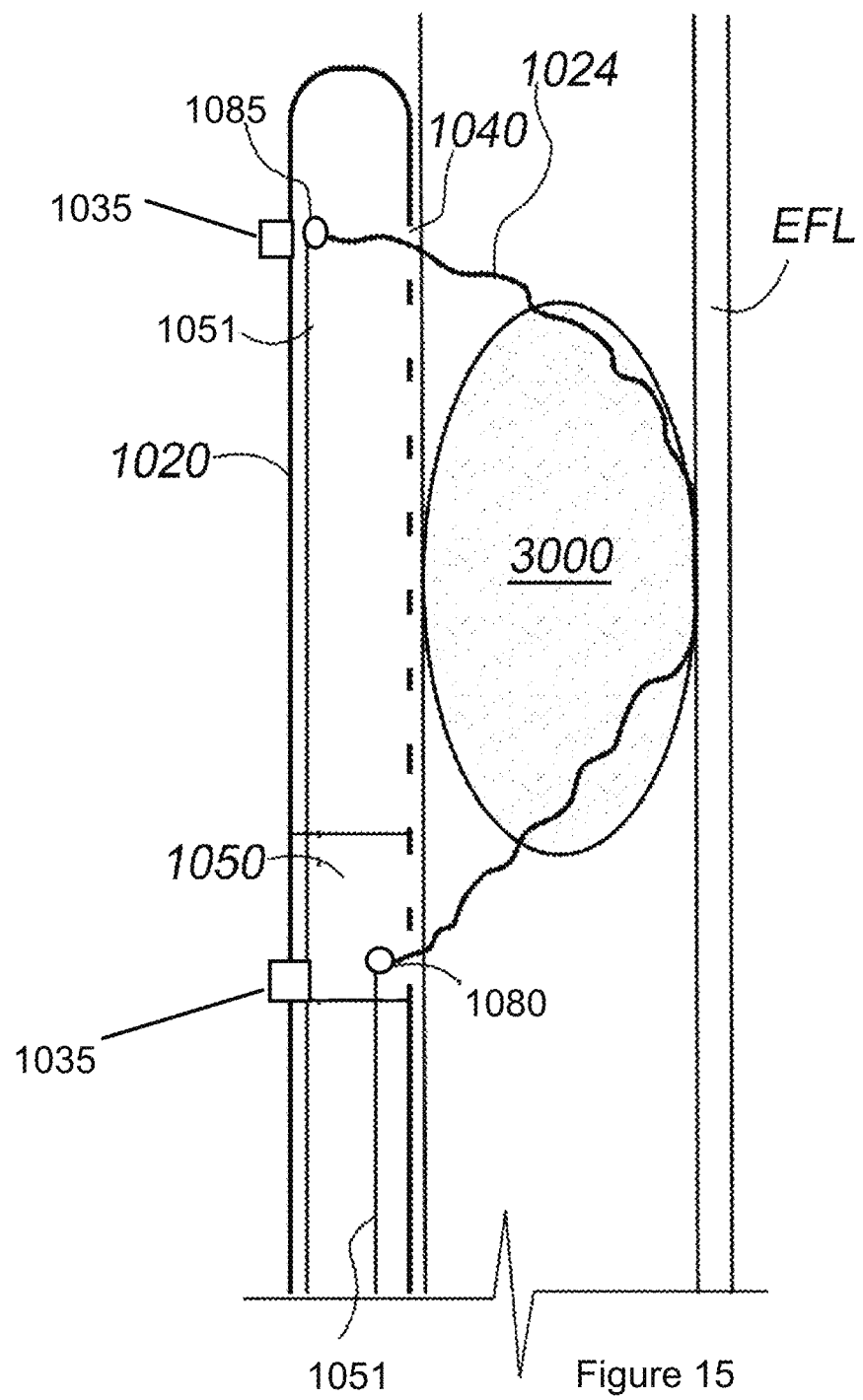
FIG. 15 shows a cross section of a hollow tube of a catheter or spline, and optic fibers therein.

In a different embodiment, shown in FIG. 15, an illuminating fiber may be replaced by one or more LED emitters 1080. In some cases a single LED emitter will output the single wavelength needed for the invention, while in other embodiments the LED's output will provide sufficient wavelengths for the calculations discussed above. In still other embodiments two LEDs will be required to practice all aspects of the present invention.

The receiving fiber(s) 1027 may still be present, or may be replaced with one or more photodetectors 1085 (for example, the epc300 by Espros). In this situation, a spectrometer may not be needed but may be replaced by the photodetector 1085 that is sensitive to the respective wavelength. Therefore, the output of the optical fibers, which have received the light from the inner wall of the heart can be detected by a photodiode for generating a detector signal and the detector signal can be processed in accordance with an algorithm as will be described below.

The number of photodetectors 1085 required will depend on the number of wavelengths to be recorded, as well as the number of locations at which the measurements will be taken.

Replacing the fibers with LEDs or photodetectors may provide a more readily rotatable and linearly translatable sensor package, as the system would not need to rotate the fibers along the entire length of the catheter, nor would it be required to move the fiber along the entire length, but rather would only need to rotate the distal portion with the LED and photodetector fixed on, for example, a shaft in the lumen. In addition, the use of photodiodes or LEDs might be advantageous in a loop or lasso type catheter due to the effect severe bends or curves could have on transmission in an optical fiber.

Offset Mechanisms

FIG. 5 shows the end-on view of the basket. In FIG. 5 each spline 1020 includes one or more emitting fibers 1028 (1028, 1028', 1028") and one or more receiving fibers 1027 (1027, 1027', 1027"). While the discussion above largely focuses on a longitudinal offset between fibers on the same spline, in another embodiment the offset is a radial offset between fibers on different splines. In such a fashion it is possible to provide larger offsets in more locations. In particular, if an ablation electrode 1050 on the topmost spline ablates the tissue adjacent to it, emitting fiber 1028 may send NIR signals to receiving fiber 1027", 1027', and even emitting fibers 1028' and 1028". Likewise, emitting fiber 1028" may send NIR signals to receiving fiber 1027, 1027', and even emitting fibers 1028' and 1028. In so doing the radial offset provides an additional depth of inquiry, and a larger pattern of inquiry to that provided by utilizing 1027' and 1028" to interrogate the tissue near electrode 1050.

Figure 18:
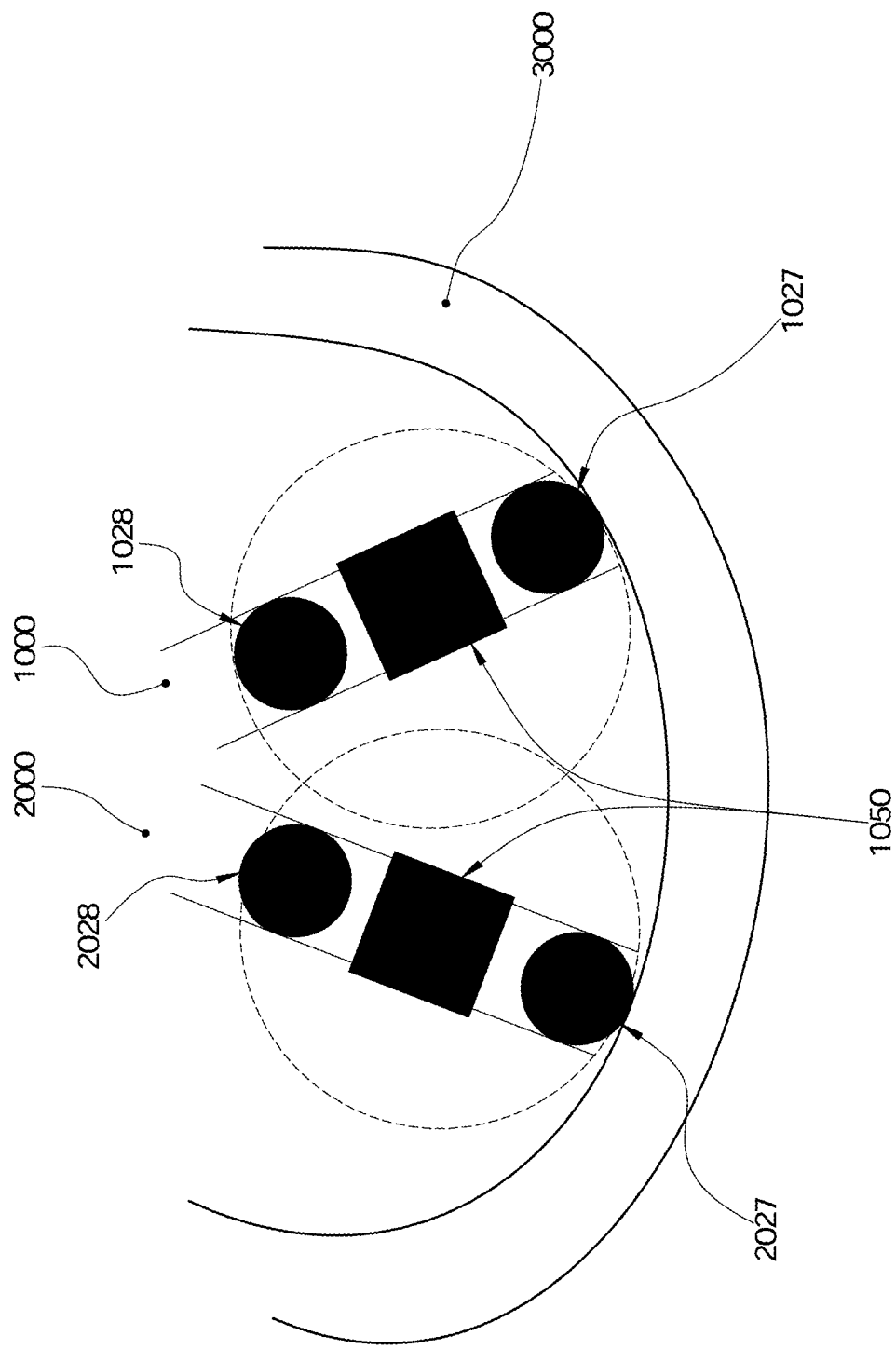
FIG. 18 shows a cross section of the catheters in a multiple catheter embodiment.

Similarly, as shown in FIG. 18, if two catheters 1000, 2000 are present, the fibers may talk to each other fiber. So, fiber 1027 may talk with fibers 1028, 2027, and 2028, again providing an increased depth and area of inquiry. The catheters 1000, 2000 may be in the same chamber of the heart or area of the body, or they may be in different chambers. Likewise, one may be in the esophagus.

Laid Alongside the Tissue and in a Stable Relationship to the Tissue

As mentioned, in addition to providing a sufficient spatial offset, it is also critical that the catheter be laid alongside the tissue, ensuring close contact between the catheter and the tissue, and that the catheter be in a stable relationship to the tissue as motion artifacts and differential contact pressure can affect the optical sensing. It is advantageous that the optical sensors not only be laid aside the tissue to be measured, but that they are in stable contact with the tissue. In particular, it is preferred that no or little blood ingress between the sensor and the myocytes. In addition, changes in the contact force can change optical characteristics.

Several mechanisms are contemplated for ensuring this contact and relationship, and it is contemplated that the user will chose which mechanisms may most synergistically work together for a particular embodiment. First, as discussed above, and as illustrated in FIGS. 2, 4, and 8, the shape of the catheter may be adapted to the anatomy it will be used in. As such a renal denervation catheter will be longer and cylindrical, while a portion of a catheter for pulmonary vein isolation may fit into the pulmonary vein to provide a stable anchor for the remainder of the catheter to ablate and examine the atrium.

In some embodiments, the invention uses diamond shaped struts to exert radial force against the tissue, e.g., with a basket catheter a diamond shaped strut (or a strut that has a portion in diamond shape) will provide a radial force against the antrum when the catheter is placed into it.

Likewise, a lasso type catheter may provide a series of fibers or other mechanisms in close, but spaced, contact with the tissue.

In some embodiments the catheter comprises biasing agents designed to orient the catheter toward a portion of the tissue, allowing it to stay in contact with the tissue during tissue movement. Biasing agents could include nitinol, an insertable stylet that is inserted to provide the catheter with a particular orientation, pull wires or another steering mechanism. In a basket catheter independent control of each spline can be utilized to increase or improve the contact individually.

In some embodiments the catheter comprises a method of holding the optical sensors in steady and stable contact with the tissue. For example, the catheter may comprise one or more hooks, barbs, or suction mechanisms designed to hold the catheter in one place despite tissue movement, and do so without substantially changing the degree of contact. A suction mechanism has the advantage of easy removal by turning the suction off.

In some embodiments it is advantageous to fix the external portions of the catheter in place to ensure stability. So, for example, the proximal catheter handle can be attached to the bed rail for immobilization/stabilization of the catheter. Likewise, the proximal shaft of the catheter can also be affixed and immobilized at the puncture site.

In an alternative embodiment, the system may employ gating to collect data from a given part(s) of the cardiac and/or the respiratory cycles. In this embodiment the system needs a means of measuring the cardiac cycle, or an input from another system that has such information, such as an EKG, an electroanatomical mapping system, or an ultrasound system. In such an embodiment the system will only base its calculations on the results taken during a specific portion(s) of the cardiac cycle, ensuring that the degree of contact is consistent for each measurement.

In another embodiment the catheter is designed so that the distal portion (or the portion with the optical sensors) is of a forgivable easily deflectable structure. As such, the distal end may be very "floppy" such that it moves freely with the tissue it is in contact with. Such a catheter may require an introducer to get through the body to the target site. In another embodiment the catheter is magnetically navigated to the target location, and as such is floppy and moves with the tissue under contact.

In another embodiment the catheter comprises force sensors at or near the optical sensors. By utilizing the information from the force sensors the system can again gate which signals it uses by the degree of contact at the signal's time. In the alternative, the system can take the degree of contact into account and correct the signal based on increased or decreased contact. The system can also warn the physician if the degree of contact gets too low or is otherwise unreliable.

This force sensing can be useful in multiple ways for certain ablation modalities (RF, Cryo, etc.) where it is necessary to maintain a certain amount of force between the ablation device and the tissue. This force changes the tissue in multiple ways, including moving it from normal anatomical position (compared to earlier MRI or CT scans), or compressing it such that the tissue thickness becomes thinner (compared to earlier MRI or CT scans).

In the context of the present invention, knowing the degree of force applied can be key to understanding how much energy has been applied, how thick the tissue is now (and thus the depth to measure as well), and the calculation of an accurate percent lesion transmurality.

To account for these force changes to tissue it may be necessary to collect real-time thickness data or include a correction factor into the algorithm, or it may be necessary to account for the contact force. For real-time tissue thickness measurement an ultrasound sensor or similar can be mounted on the same structure as both the optical sensor and the ablation electrode, or it can be mounted with only the optical sensor. If it is mounted only with the optical sensor, and a single point ablation catheter is used, it may be necessary to use data from an electroanatomical mapping system to calculate the relative distance between the electrode next to the ultrasound and optical sensors, with respect to the tip electrode on the ablation catheter. This may need to be done because the ablation catheter may push tissue away from a sensing only catheter, at least slightly.

Multi Electrode Catheter

Figure 17:
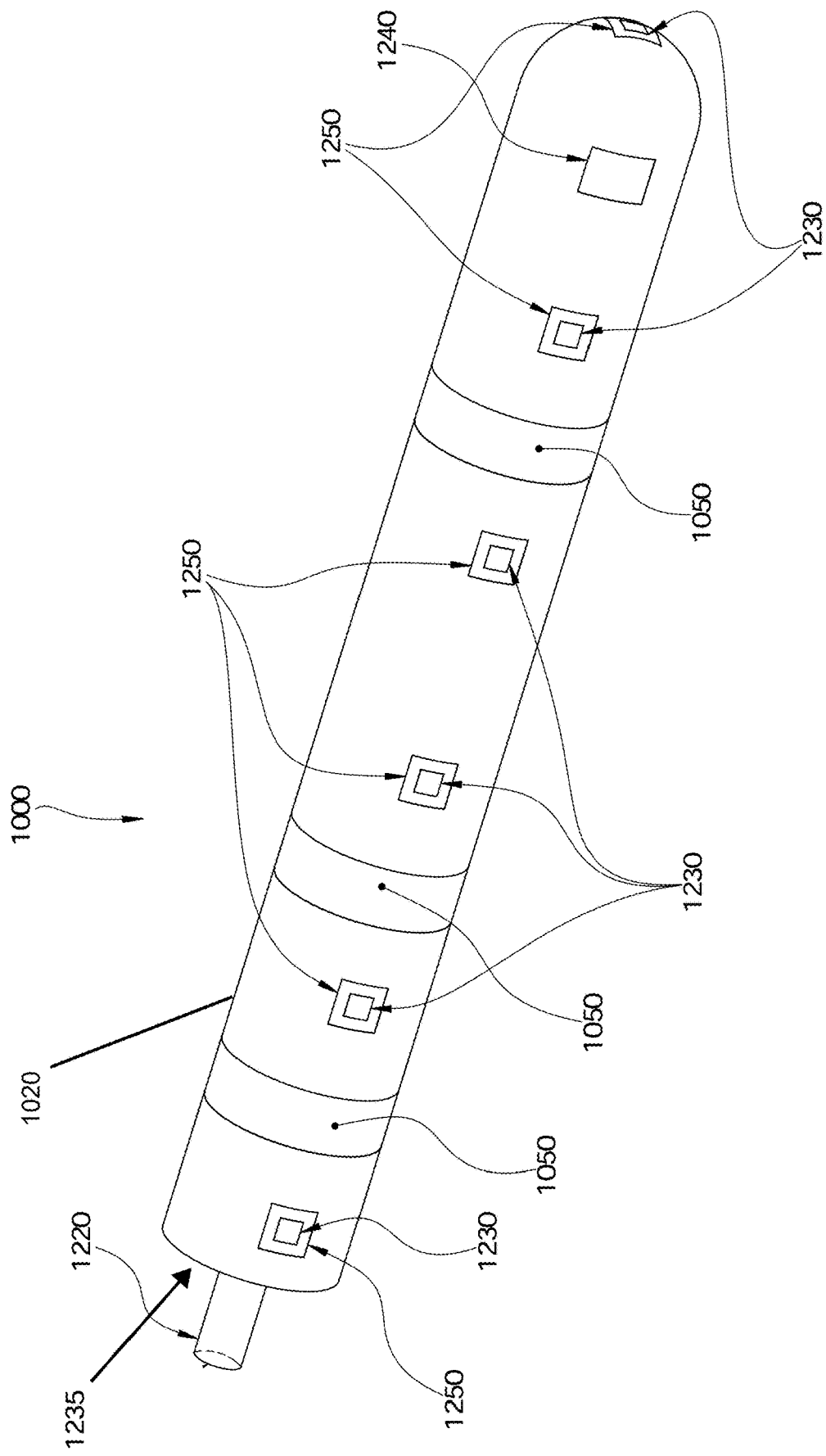
FIG. 17 shows a cross section of a hollow tube of a catheter or spline, and optic fibers therein.

In another embodiment, the catheter 1000 can be a loop, basket, or similar catheter with multiple electrodes 1050, as shown in FIG. 17. The catheter has at least one open lumen 1235 in its shaft 1020. This lumen provides access to a window 1250 next to each electrode. Windows 1250 may also be provided in an electrode. In an alternative embodiment, the distal shaft (or portions thereof) is optically transparent at the relevant wavelengths, and windows are not needed.

A torque shaft 1220 with NIR sending/receiving elements 1230 mounted at its distal portion is inside lumen 1050. The torque shaft may also have an ultrasound element 1240 added for anatomical characterization. This torque shaft can be rotated by the user, by hand, or by motor, to eliminate any angulation issues which might typically come from hard mounted sensor in a fixed position on a catheter.

The NIR sending/receiving elements 1230 may comprise fibers, or alternatively may comprise a combination of LEDs and photodetectors. Preferably the torque shaft 1220, elements 1230, and associated materials are manufactured together as an assembly 7000 or as multiple assemblies. Providing an assembly 7000 results in a simpler calibration, a lower cost device, and a more flexible device.

There are multiple diagnostic assembly types that may be utilized in any of the catheter embodiments disclosed herein. For example, the diagnostic assembly may be as simply as an emitting element and a receiving element spaced apart along the longitudinal axis of a catheter portion, such as a distal portion of a linear catheter, the loop of a lasso style catheter, or a spline in a basket or ray catheter. The assembly may be embedded in a catheter wall or placed in a lumen, and may be rotatable with, or separately from the catheter.

In another embodiment, the diagnostic assembly can include an insert, typically placed in the catheter or a catheter lumen for delivery to the diagnostic location. In some embodiments the diagnostic assembly may exit the lumen during the procedure. Preferably an insert is rotatable such that the emitter or receiver scans the tissue. Likewise, multiple inserts may be present, and one may be axially translatable relative to the other to adjust the offset, preferably along the longitudinal axis of the assembly, but at a minimum to adjust the depth of penetration on a targeted tissue. As an example, an emitter may be present in a first insert, controlled by a first rotation mechanism and a first axial positioning mechanism, while a second insert includes one or more receivers and is controlled by a second rotation mechanism and a second axial positioning mechanism. It is also possible that the rotation in both inserts be controlled by the same mechanism to ensure they are lined up.

Rotating the torque shaft with fibers mounted to it, along with anatomical data from an onboard ultrasound sensor 1240 or registered to an imported anatomical data set can allow for the creation of a real-time 3D or 2D cross-section image of the lesion being formed, with a software generated demarcation of the tissue boundary and lesion boundary. This type of device may be made with one set of sensors that is moved from one electrode to the next (not shown), or sensors at each electrode as shown. A single set of sensors for interrogating one lesion set at a time will allow for that one set of sensors to be higher in number, increasing morphological, electrical, and spectral/biological resolution. Spatial offsets need to be set at distances that will not encumber assessment of transmurality over the full circumference of the PVI lesion sets. The use of LEDs and photodetectors have special advantages when the catheter must make sharp bends that could cause signal losses in a fiber optic.

In another embodiment, instead of spinning the sensors a phased array configuration may be used. There can be both multiple ultrasound and multiple optical sensors arranged to point into the tissue at multiple angles on a single structure. In this way the need for spinning the sensors to get a (largely) 2D planar slice is not necessary. To get a fully 3D image of the entire tissue region however, one must move the imaging sensors along the axis of the device, or in a similar fashion to the previous teaching, sensors can also be arranged over a length of the device's axis.

A rotating or phased array type of sensing is optimal for multiple reasons. One reason is that it eliminates the need for compromises on angulation of the optical sensor with tissue. Ideally the sensor is aligned perpendicular to the tissue. It will in general though be difficult to implement this in a catheter that does not interrogate multiple angles because every anatomy is different.

Single Point Catheter

In one configuration, with reference to FIG. 19, an irrigated ablation catheter 1000 has a single fiber 1026 (transmitting and/or receiving) or multiple fibers 1026. In the alternative the irrigated ablation catheter 1000 may have an LED or a photodetector, as per above. This fiber works with one or more fibers 1026 located in a second catheter 2400, or in the alternative one or more LEDs or photodetectors in the second catheter.

For example the transmitting optic fiber 1026 can be in the ablation catheter 1000 and the receiving optic fiber 1026 can be embedded in the second catheter 2400. Location sensors, such as magnetic coils, markers, or electrodes on each catheter are used to track relative position, which is then input automatically into the algorithm to aid in calculating transmurality. In this configuration ablation could be either unipolar or bi polar. In this configuration the catheter separation/offset can be easily adjusted to gain additional information, it can be used to create point by point lesions, and allow the user to use multiple catheters configurations that they are familiar with.

Alternatively the single point catheter may incorporate both transmitting and receiving fibers with an electrode between them. In one embodiment the distal tip of the catheter would have a preferential bend 1300 to dispose the optical elements and electrode(s) to the tissue in the correct orientation. It is expected that the distal tip of such a catheter would have an L shaped end. Alternatively an L shaped catheter like the above may have multiple transmitting or receiving fibers 1026 only. It is meant to be used in conjunction with a single point ablation catheter incorporating a single fiber. In use, the L shaped catheter tip points toward the single point ablation tip, such that it places optical components at different distances from the ablation catheter tip.

Instead of an L shape, the catheter may take other forms that dispose the fibers along the tissue. For example, the catheter may take an S shape, or other curve, that places the fibers along the length of the tissue. If the catheter is able to enter the cavity at the correct orientation, the catheter may also simply lie straight as its placed on the tissue. In an alternative embodiment the catheter forms a triangle, with, for example, two halves separating or opening up to have a perpendicular strut between them at the distal end. This perpendicular section in operation is laid on the tissue. It would include any required ablation elements, sensors, and the fiber optics for the present invention.

Loop/Ray Catheter

In some embodiments the catheter 4000 is adapted to fit the targeted anatomy. For example, as shown in FIG. 20a, the catheter may comprise a relatively straight shaft 4010 that turns 90 degrees at a distal portion and forms a loop 4020 that is orthogonal to the shaft. The catheter may have multiple fibers 4026 arranged around the loop and may optionally have an ablation electrode 4080. In use, the loop is pushed to the target tissue. The ablation electrode may be used to ablate, while the fibers are used to sample the tissue in any combination that provides a sufficient examination of the target tissue. Likewise, if a second catheter is used, the loop may form a ring around that second catheter's ablation electrode. Preferably the loop comprises markers, location sensors, or another means of determining location. In particular, the system preferably knows the location of the fiber ends for its calculations, and accordingly such markers or sensors should be near or on the terminal fiber ends.

In a similar embodiment to that shown in FIG. 20*a*, the catheter may have a second loop that is parallel to the first loop. Ablation is typically performed with an ablation catheter between the loops. Each loop will have electrodes by each optical sensor for positional tracking and input into the optical sensing algorithm. Each optical emitter will have its own time dependent frequency or carrier wave frequency, such that light received from each optical receiver can be differentiated between each emitter, for calculation of lesion shape.

Figure 20B:
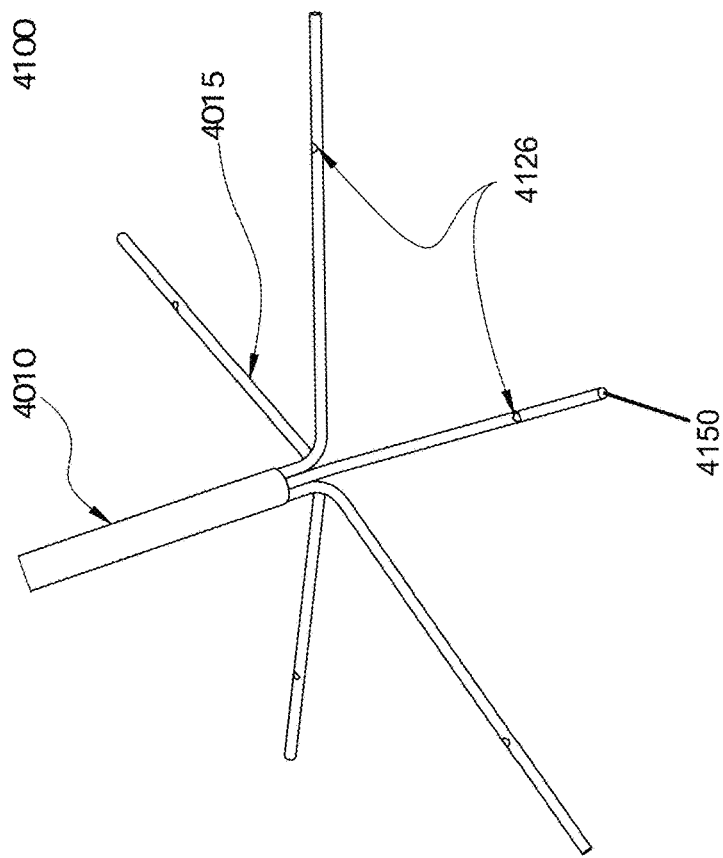
FIG. 20b shows a cross section of one catheter embodiment of the present invention.
Figure 20A:
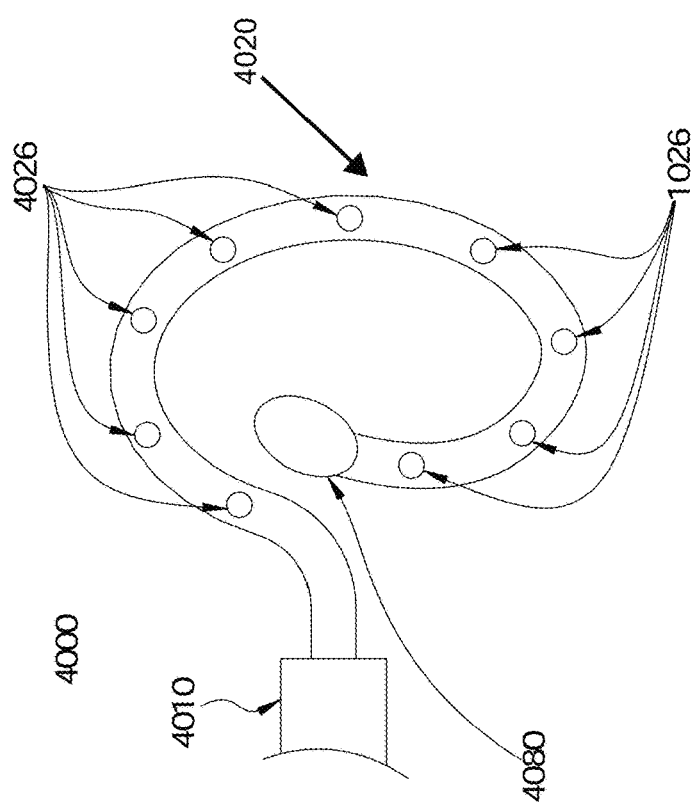
FIG. 20a shows a cross section of one catheter embodiment of the present invention.

As shown in FIG. 20*b*, a similar catheter 4100 comprises a relatively straight shaft 4110 that separates into multiple splines 4015 at a distal portion. The splines may be relatively free floating, and only attached at their proximal ends to the distal end of the straight catheter shaft 4110. In this manner the splines, when pushed to a target tissue, may conform to that tissue with a more consistent level of contact force. The catheter may have multiple fibers 4126 arranged on the splines 4015, and may optionally have an ablation electrode 4150. In use, the splines are pushed to the target tissue. The ablation electrode may be used to ablate, while the fibers are used to sample the tissue in any combination that provides a sufficient examination of the target tissue. Likewise, if a second catheter is used, the splines may surround that catheter's ablation electrode. The splines may also be relatively stiff in some portions, e.g., at their proximal ends to keep them oriented apart, but flexible in a distal portion to conform to the anatomy. Preferably the distal end comprises markers, location sensors, or another means of determining location. In particular, the system preferably knows the location of the fiber ends for its calculations, and accordingly such markers or sensors should be near or on the terminal fiber ends.

As shown in FIGS. 20*c*, 20*d*, and 20*e*, various other loop or ray catheter configurations are possible. Such catheters may comprise a shaft portion 4200, a sensor portion 4210 configured to contact the tissue 3000, and may include a stabilization portion 4280 designed, for example, to hold the catheter in a particular location. For example, stabilization portion 4280 may fit within a pulmonary vein to hold the catheter in place at the vein.

Basket Catheter

Figure 4:
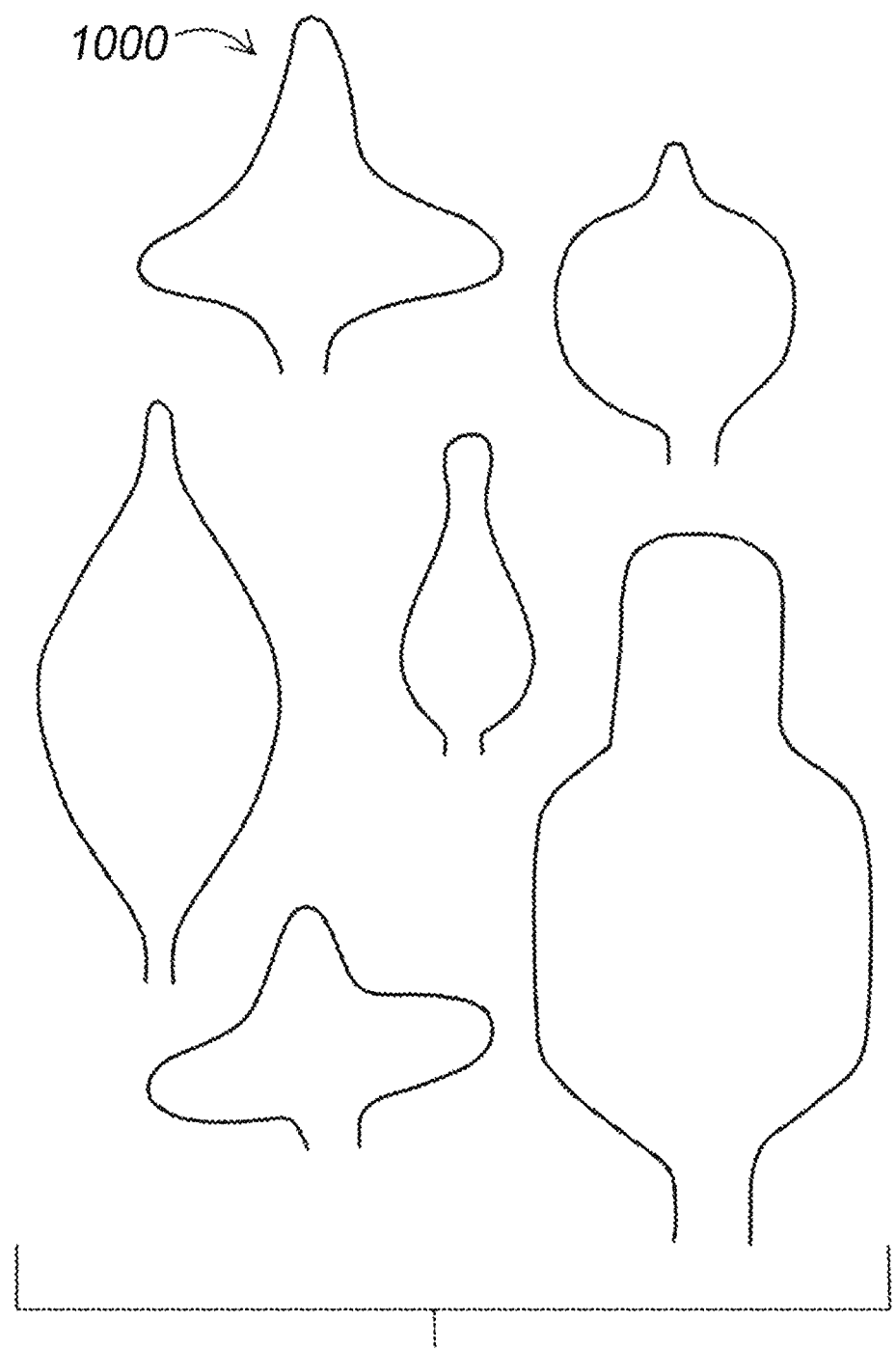
FIG. 4 shows alternate shapes for a basket configuration.
Figure 21:
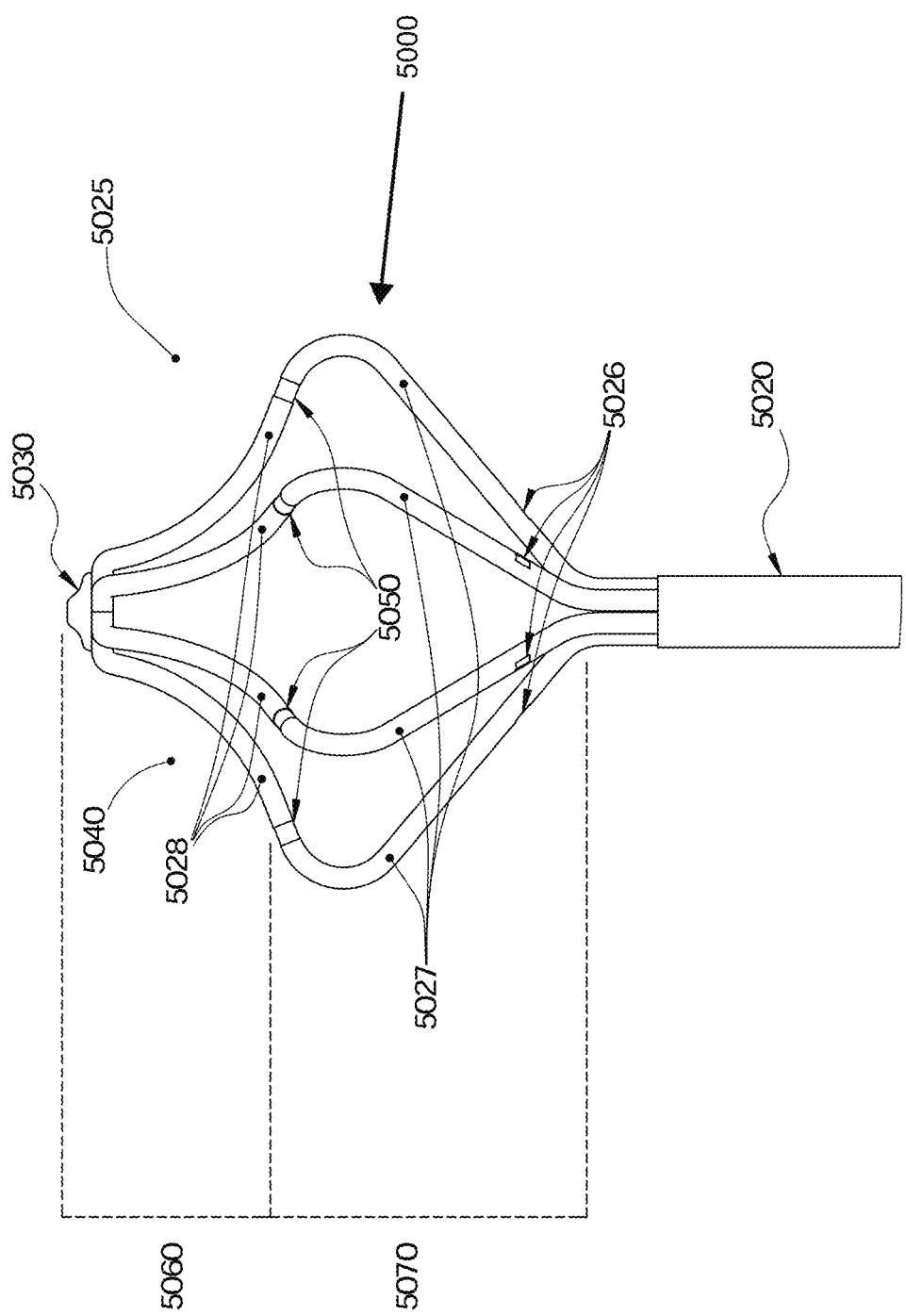
FIG. 21 shows a cross section of the one catheters of the present invention.

With reference to FIG. 4, in some embodiments the catheter 1000 is adapted to fit the targeted anatomy. For example, as shown in FIG. 4, a basket catheter may take a shape that is not a normal oblong shape, but rather forms a basket that has a more narrow distal region and a wider proximal region. Thus, with reference to FIG. 21, a catheter 5000 may comprise a relatively straight (but preferably steerable/bendable/curved to fit the anatomy) shaft 5020.

The distal end of the shaft comprises a basket or balloon 5025. At the distal most portion of the basket 5025 is an atraumatic tip 5030. The basket comprises struts 5040. In a preferred embodiment the distal portion 5060 of the basket is more narrowly sized and shaped to securely fit within a pulmonary vein. Ensuring a proper fit in the pulmonary vein allows the catheter to hold its electrodes 5050 outside of the pulmonary vein. The proximal basket catheter portion 5070 is wider than the distal portion 5060 and resides in the atrium, and stays largely outside of the vein. As the splines or struts 5040 are flexible, the basket can adapt to irregular anatomy.

The electrodes are spaced apart. In one embodiment, the distal portion 5060 has a sufficient number of struts that, at the ostium of the pulmonary vein, the struts (and thus the electrodes, are spaced 10 mm apart. In order to fit a typical 30 mm diameter antrum, the catheter would need 10 electrodes at 10 mm apart. In another embodiment the struts 5040 are 5 mm apart, and thus for a similarly sized antrum would have 20 electrodes.

Each strut further has optical fibers 5027, 5028, and 5026. The number of optical fibers on each strut may vary, but it is preferred that there are at least two fibers on each strut, and preferably one on each side of the electrode. In use, the optical fibers (e.g., 5027) on a first strut can transmit to or receive from any other optical fiber 5026, 5027, or 5028 on the basket catheter 5000, or on any other catheter. In another embodiment, the optical fibers are movable and rotatable, as described herein. In a preferred embodiment, markers near or on the terminal ends of the fibers 5026, 5027, 5028 allow the system to know the precise location of the fiber, and accordingly calculate the offset for each fiber pair. The fibers may be replaced by other emitters (e.g., LED) and detectors (e.g., photodetectors) as needed.

Preferred optical sending and receiving components are placed at varying distances from each other, e.g., 2 mm part, 5 mm apart, 10 mm apart, 20 mm apart, or up to 30 mm apart. The distance will depend on the anatomy to be scanned. The distance between two splines depends on the application. In one embodiment the distance is about 6-10 mm separation, so optical elements from two adjacent basket splines can interrogate ablation transmurality between splines. This can be ideally done in an X pattern, or between just one transmitting element (LED, fiber, fiber w/prism, fiber w/mirror) from one spline, to one optical receiving element on an adjacent spline.

In another embodiment, the basket further comprises a basket pull wire that can be activated to increase or decrease the basket diameter. Alternatively, a shaft in the basket catheter, for example a middle shaft, could be advanced or withdrawn to adjust the shape and size of the basket. Such a shaft could also be used for irrigation. The basket catheter may further comprise force sensors to determine when the basket is fully seated within the pulmonary vein, or when the proximal portion is properly in contact with the antrum or atrium, as desired.

The basket catheter can have splines that are designed to move directly north and south, perpendicular to the tissue, similar to the splines depicted in FIG. 2, or splines that move in another fashion, e.g. a sinusoidal fashion.

Figure 24:
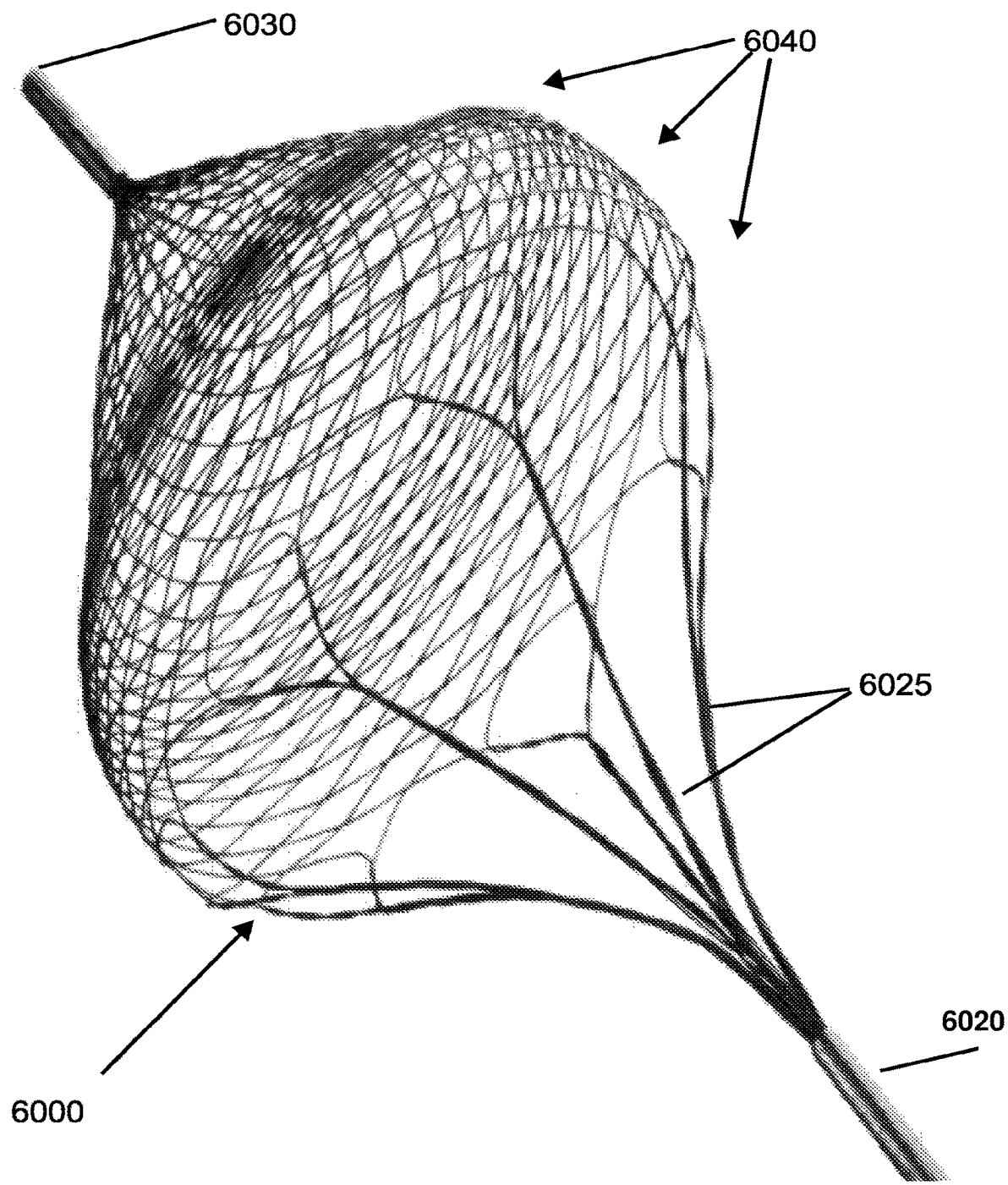
FIG. 24 shows a basket catheter according to the present invention.

FIG. 24 shows an alternative catheter in a mesh basket design. Catheter 6000 includes a shaft 6020, splines 6025, mesh region 6040, and atraumatic tip 6030. The mesh region 6040 includes numerous fiber optic probes. For example, a fiber optic probe (and aperture or mirror, as required) could terminate at each joint pictured, or at the space between each joint.

Alternatively, fiber optic probes terminate in a specific region of the mesh. In use the mesh is meant to conform to the tissue, providing numerous fiber optic sites that are in stable contact with the tissue.

System

In one embodiment the invention comprises a system. The system includes a catheter, as described herein, a light source connected to the catheter, e.g., to one or more fiber optics, a spectrometer, an optical multiplexer, a computer, and an output mechanism, such as a display.

Figure 12:
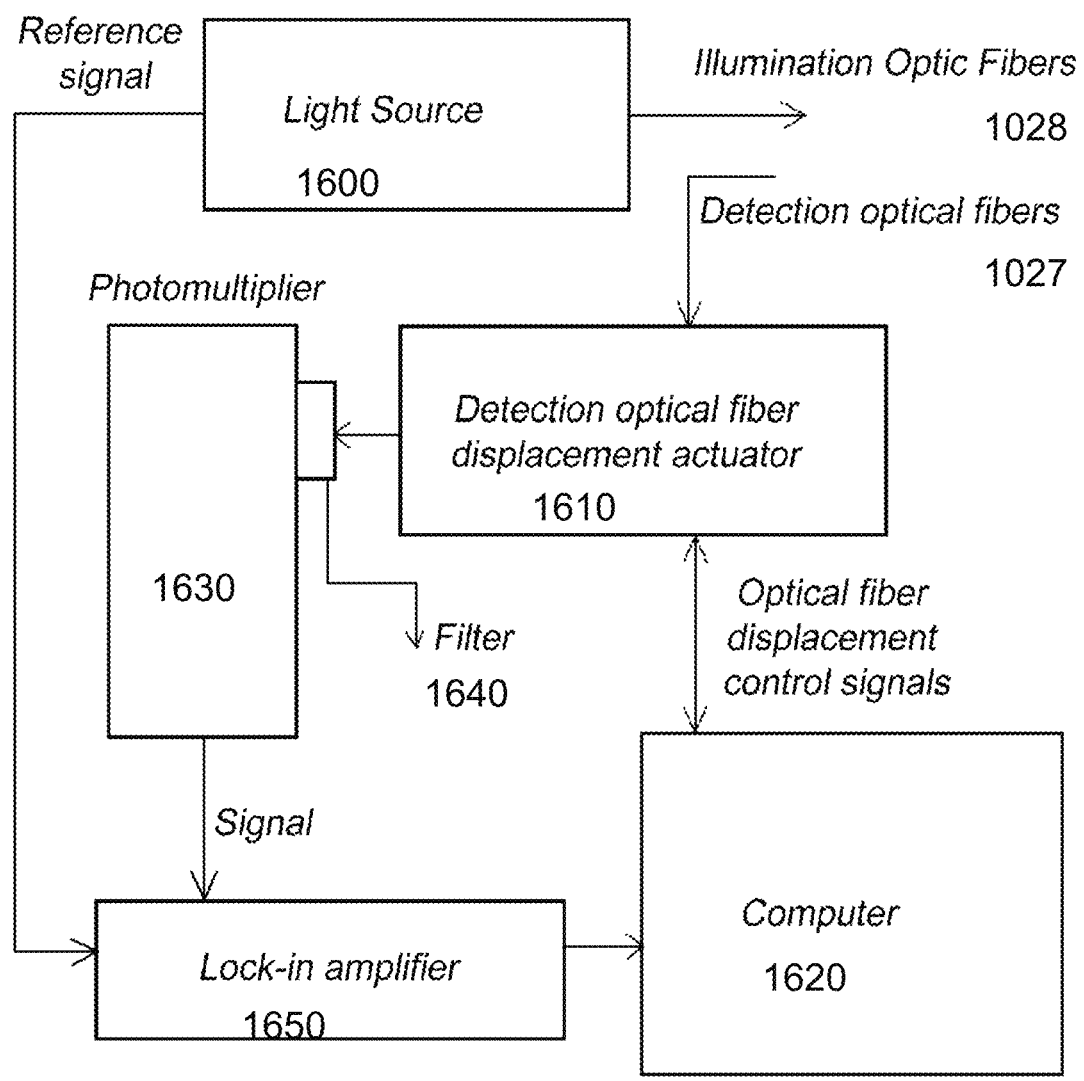
FIG. 12 is a schematic view depicting components of a system of one embodiment according to the present invention.

As shown in FIG. 12, a light source 1600 delivers light through illuminating or transmitting fibers 1028 on the catheter. The light passes through the tissue, is scattered, and then reemerges. The amount of light at different frequencies which reemerges is dependent on the type and amount of tissue it has penetrated. The light is received by the receiving optical fiber 1027. The light may be sourced as or processed according to Near Infrared, NIR, Raman, Fluorescence spectroscopy, birefringence, and OCT to collect depth data, The receiving optical fiber 1027 may be displaced in two ways, as discussed above, by the detection optical fiber displacement actuator 1610, which may be controlled by a computer 1620 or other control mechanism. First, it can be rotated by the user, by hand through a shaft or actuator, by galvanometer or by motor. Second, it can be linearly translated through a range of a linear distance to increase or decrease the offset. Each of these displacement actuator mechanisms 1610 can adjust the location or depth of scan.

The light received by the detection optical fibers 1610 are received by a sensor, such as photomultiplier 1630. In some embodiments the light is processed by a filter 1640 or other mechanism and may be amplified 1650 as needed before being processed by a computer 1620, which may be the same or different than the above processor.

The software can monitor one electrode at a time, or multiple electrodes. Likewise, the software can monitor one fiber pair or multiple fibers, in pairs or other combinations.

In some embodiments the software only monitors the ablation or the tissue. In others, the software would control ablation for one electrode or multiple electrodes. The software can stop the ablation before a full ablation is completed, including to prevent complications or over ablation, and allow the physician to incrementally add ablation time to complete each lesion. The latter would be an initial safety precaution to keep from over ablating. In other embodiments, the system can simultaneously control all electrodes.

Safety controls can be implemented in some embodiments, such as allowing ablation to proceed automatically to 90% complete, and then requiring physician input or control to continue. Likewise, with a robotic system or a magnetically manipulated catheter system, the control system can move the catheter and ablate automatically.

The system can also measure the thickness of the tissue, or receive input from another system that does so, such as a CT scan, MRI, or the like. These can be imported, scaled and 3D registered to fit with an anatomic map that is made for each case with a system similar to NavX, Carto 3, or Local Lisa.

Once such an endocardial surface chamber anatomical map is created and the tissue thickness data is imported and registered, then the same anatomical mapping system can localize each of the ablation catheters electrodes such that the tissue thickness below each electrode and between electrodes is known within a reasonable tolerance. To optimize the understanding of tissue thickness below each electrode an optical method may be used. This optical reading may be synced with the reading from the other system, registered to the map from another system, or used in a calibration of the optical measurements to be used throughout the procedure.

To measure tissue thickness fibers with multiple offset distances will be required on each spline, or two fibers with an adjustable offset. The NIR sensing method is most efficient at measuring tissue constituents rather than mapping anatomy, but can be effective for localized mapping.

Another option to more accurately understand tissue depth prior to ablation start would be to measure the tissue thickness with on-board ultrasound sensors at each electrode or a separate ultrasound catheter/tool. Within the software a calibration interrogation using the present invention should take place prior to ablation, after the catheter is placed in its location around the antrum of the pulmonary vein. This calibration data and thickness data is then combined to provide a starting point for lesion creation. Alternatively, additional data can be added to the algorithm to more precisely determine transmurality. As an example, in most EP procedures, electroanatomical maps are created. These maps can help the user understand the location of viable myocytes versus scar, which might help refine the NIR calibration inputs.

In the procedure, lesion formation can be done with either unipolar or bi-polar methods, and may be adjusted as necessary with inputs from the present invention. Calibration spectral analysis may be used to determine apposition and or sensor/electrode forces on the tissue. The algorithm may also use heartbeat and respiration gating or adjustments to account for tissue movement with respect to the sensors.

The algorithm will ideally take and include input variables for electrode and sensor positional data from an electroanatomical mapping system, because there will inevitably be variations in distances between emitting and receiving sensors, such as when a PV antrum is small and the basket only opens to half of the possible diameter. The system can also incorporate single point positional information and alert the physician when the catheter is in optimal positional and angle orientation placement between optical sensing pairs. This optimal position may vary depending on variations in tissue thickness.

Depending on the device design it may be necessary for the fiber ends to be spaced from the electrode edge at least the same distance as the maximum tissue depth. In this way the light, as it initially enters the tissue, does not need to travel through partly ablated tissue. This should improve SNR of sensing true transmurality. However, a spacing of +10 mm for emitting to receiving fibers for use in 5 mm tissue, may not be appropriate for thin tissue, like 1 mm thick. For this reason it may often be necessary to mount multiple fibers at different distances from the electrodes.

The present invention can utilize the catheters disclosed above to create a sensing array, whether it be from multiple catheters or from one catheter with multiple optical sensors and emitters. In these configurations the sensor array is placed in the area of interest, such as an antrum to a pulmonary vein. The sensor array can find the boundary of the ablations lesions and guide the operator to place the ablation catheter in a spot within the array that will allow for, and confirm, connection of ablation lesions. The array also allows for sensing at different offsets, which allows for a more detailed sensing analysis. Each emitting source may have its own carrier wave frequencies, such that a receiving optical sensor can distinguish direction. Such a sensor array can be magnetically enabled for consistent apposition. This type of array can also be used for confirming ablation lesions and connections after isolation is believed to be complete. Such a configuration, as with some of the others can be used in an epicardial or combined epicardial/endocardial fashion.

Graphical Interface

In one embodiment, the system of the invention is designed to work with a graphical interface. The graphical interface may be a standalone interface designed for use in the present system, or the present system may interface (or patch into) an existing graphical interface such as an electroanatomical mapping system, an ultrasound system, a fluoroscopy system, or an MRI system.

As detailed above, constant and consistent contact is desirable. The system may graphically alert the operator if the degree of contact has changed, has become insufficient, or has become excessive. Such alerts can be an audible alert, tactic feedback, computer visual output on a real time map, e.g., on an electroanatomical map or on a previously generated map, e.g., a MRI taken earlier.

As part of the GUI it may be ideal for the image created by a mapping system to present a lesion progression line created from the system's data and over laid onto the mapping image. Alternatively, the remaining viable tissue at a lesion can be represented in an alternative distinctive color. In this case the user will attempt to eliminate the viable tissue color. Preferably the lesion progression line is three dimensional, that is it not only shows the location of the lesion as a 2 dimensional overlay on top of the tissue, but it shows the depth of the lesion as it progresses.

The GUI may allow the user to orient the image in any 3D representation, including scaling and allowing the user to view the extent of the lesion, the tissue thickness. For example, the GUI could color code different tissue thicknesses, or tissue types, to render decision making easier.

Cryo Ablation Balloons/Devices

The optical transmitting/receiving elements can also be mounted to balloons and other cryoablation devices. In use however, the software algorithm may need to be modified since the cellular and extracellular ice formation changes the optical response. As a result, the software and GUI will need an input mechanism to indicate the type of device being used. Such input may be manual by the operator, or may be an automatic recognition by the software, via an EEPROM or another means. Fibers may be mounted directly to cryo balloon catheters. These balloons are compliant and may be adjusted in pressure to apply both the appropriate force for ablation and for sensing.

Manufacturing

Figure 25:
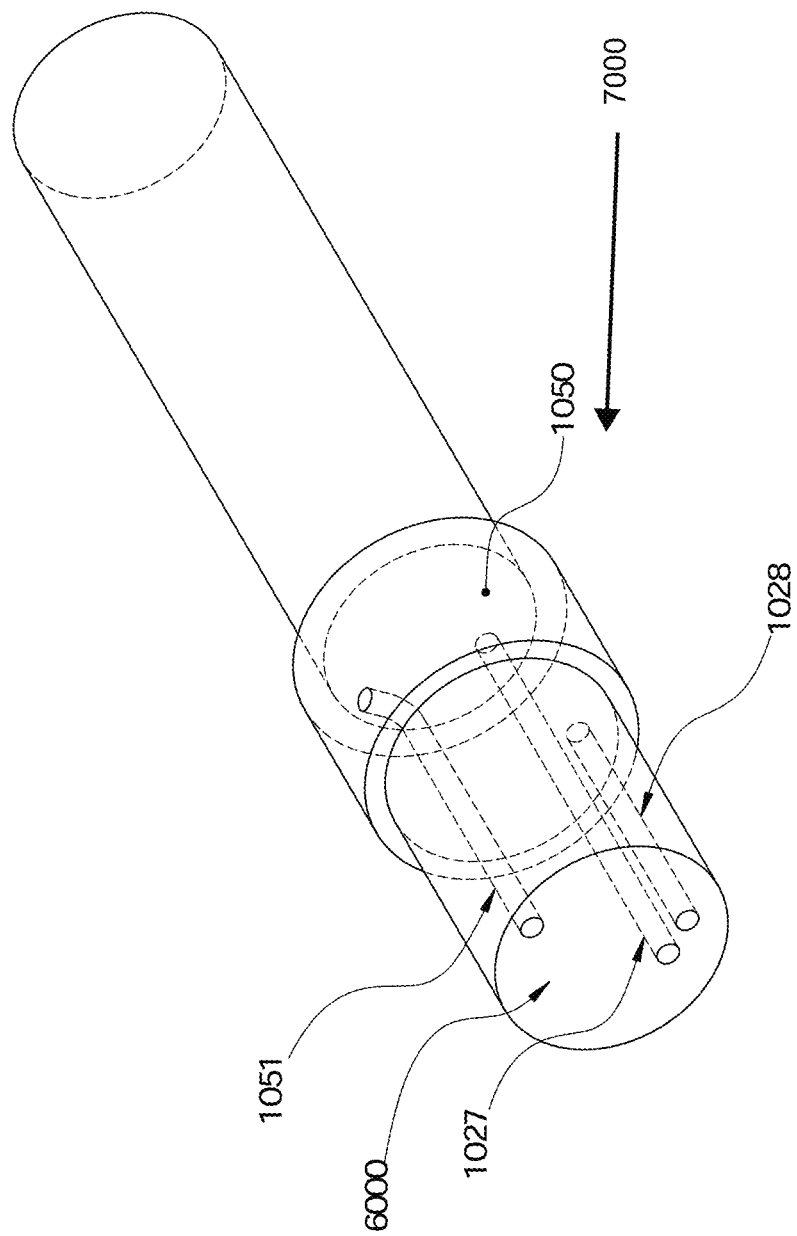
FIG. 25 shows a 3d modeled insert according to the present invention.

For ease and cheap cost of manufacturing-optic fibers can be inserted into 3D printed part. As shown in FIG. 25, a 3D printed part may be prepared with the relevant lumens and exit ports. Receiving and optic fibers are inserted into the "side by side" channels with the transmitting optic fiber inserted into the shorter channel and the receiving optic fiber inserted into the longer channel. The top channel is for the copper wire to the electrode. Providing a 3D printed part allows for ease of manufacturing, and controls the fiber optic manufacturing to prevent breakage. An insert that holds the fiber optics (whether 3D printed or otherwise) can also provide for ease of rotation of the sensing assembly 7000, and avoid fiber optic twisting or breakage.

In view of the many possible embodiments to which the principles of the disclosed invention may be applied, it should be recognized that the illustrated embodiments are only preferred examples of the invention and should not be taken as limiting the scope of the invention. Therefore, this disclosure is intended to cover such alternatives, modifications, and equivalents as may be included in the spirit and scope of the description in view of the appended drawings and claims.

I claim:

1. A system for monitoring tissue comprising:
a catheter, the catheter having an elongated body member having a proximal end and a distal end;
a biasing element in the distal end, the biasing element configured to bias the distal end into contact with a first tissue portion,
wherein the distal end includes:
an optical emitting element, the optical emitting element oriented to emit optical radiation into the first tissue portion,
an optical receiving element oriented to collect optical radiation, the optical radiation indicating characteristics of the first tissue portion;
wherein the optical receiving element and the optical emitting element are arranged to be spatially offset along a first longitudinal axis of the distal end, and along the face of the first tissue portion, and
a workstation, the workstation comprising
an optical radiation analysis module stored in a memory and executed by a processor, configured to process the optical radiation collected by the optical receiving element using spatially offset diffuse reflectance spectroscopy, wherein the processing element is configured to calculate the rate of denaturation of the tissue adjacent to the distal portion.

2. The system of claim 1 wherein the biasing element comprises a biasing shape, a retention means, a steering means, a nitinol element, or an insertable stylet.

3. The system of claim 1 wherein the distal end further comprises a first aperture, and wherein the optical emitting element is configured to emit optical radiation through the first aperture into the first tissue portion.

4. The system of claim 3, wherein the distal end further comprises a second aperture, wherein the optical receiving element collects radiation that enters through the second aperture.

5. The system of claim 1, wherein the distal portion comprises a basket assembly, the basket assembly comprising a plurality of radially expanding splines adapted to position a first spline adjacent a tissue, the first spline including the optical emitting element and the optical receiving element.

6. The system of claim 5, further comprising a second spline with a second longitudinal axis, the second spline comprising:
a second biasing element adapted to position the second spline adjacent a second tissue portion,
a second optical emitting element configured to emit optical radiation into the second tissue portion,
a second optical receiving element configured to collect optical radiation, the optical radiation indicating characteristics of the second tissue portion during the application of energy to the second tissue portion;
wherein the second optical receiving element and the second optical emitting element are arranged to be spatially offset along the second longitudinal axis of the second spline.

7. The system of claim 1 further comprising a spatial offset displacement actuator configured to adjust the spatial offset between the optical receiving element and the optical emitting element along the first longitudinal axis such that the spatial offset between the optical receiving element and the optical emitting element is adjustable.

8. The system of claim 1, further comprising an electrode configured to apply energy to the first tissue portion.

9. The system of claim 1, wherein the processing element is configured to generate an optical spectra of the optical radiation collected by the optical receiving element.

10. The system of claim 1, wherein the processing element is configured to compare the processed optical radiation collected by the optical receiving element to a reference optical radiation for at least one of following tissue types: fat, nerve, muscle, or collagen.

11. The system of claim 10, wherein the processing element is configured to determine that adjacent tissue is at least one of the following tissue types: fat, nerve, muscle, or collagen based at least on the comparison between the generated optical spectra and the reference optical spectra.

12. The system of claim 9, wherein the processing element is configured to compare the generated optical spectra of the optical radiation collected by the optical receiving element to a reference optical spectra for tissue fluid.

13. The system of claim 1, wherein the processing element is configured to directly or indirectly control an ablation electrode based on a rate of thermal denaturation of the first tissue portion.

14. The system of claim 1, wherein the processing element is configured to extract a rate constant for the rate of denaturation of the first tissue portion.

15. The system of claim 14, wherein the processing element identifies when the tissue adjacent to the first radially expanding spline is sixty three percent denatured.

16. The system of claim 1, wherein the system determines the characteristics of a lesion, nerve, or tissue based on the rate of thermal denaturation of the tissue.

17. The system of claim 1, wherein the denaturation is a heat denaturation, a cold denaturation, or a mechanical denaturation.

18. The system of claim 1, wherein the spatial offset between the optical receiving element and the optical emitting element is at least 10 mm.

19. The system of claim 6, wherein the catheter is connected to an optical radiation source configured to provide optical radiation to the first and the second optical illuminating elements such that the first and the second optical illuminating elements substantially simultaneously emit optical radiation.

20. The system of claim 1, wherein the system determines the characteristics of a lesion, nerve, or tissue based on the optical reflectance from the tissue.

21. The system of claim 1, wherein a processing element identifies when the tissue adjacent to the distal end is transmurally denatured based on a change in the slope of a reflectance curve.

* * * * *